United States Patent
Searle et al.

(10) Patent No.: US 9,375,529 B2
(45) Date of Patent: Jun. 28, 2016

(54) EXTENDED USE MEDICAL DEVICE

(75) Inventors: Gary Searle, Norfolk, MA (US); Keith N Knapp, Warwick, NY (US); Roman Tunkel, Arlington, MA (US); Peter Skutnik, Midland Park, NJ (US); Lionel Vedrine, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1476 days.

(21) Appl. No.: 12/585,061

(22) Filed: Sep. 2, 2009

(65) Prior Publication Data

US 2011/0054390 A1    Mar. 3, 2011

(51) Int. Cl.
*A61M 5/168*    (2006.01)
*A61M 5/142*    (2006.01)
*A61M 5/172*    (2006.01)
(Continued)

(52) U.S. Cl.
CPC ......... *A61M 5/14248* (2013.01); *A61M 5/1723* (2013.01); *A61M 5/3134* (2013.01); *A61M 5/1413* (2013.01); *A61M 5/14224* (2013.01); *A61M 5/16886* (2013.01); *A61M 5/385* (2013.01); *A61M 5/46* (2013.01); *A61M 2005/14268* (2013.01); *A61M 2005/1585* (2013.01); *A61M 2005/16872* (2013.01); *A61M 2209/045* (2013.01); *A61M 2230/201* (2013.01)

(58) Field of Classification Search
CPC .............. A61M 5/3287; A61M 5/46; A61M 2005/1585
USPC .................................. 604/66, 151, 156–159
See application file for complete search history.

(56) References Cited

U.S. PATENT DOCUMENTS 3,857,382 A    12/1974    Williams, Jr. et al.
3,963,380 A    6/1976    Thomas, Jr. et al.
(Continued)

FOREIGN PATENT DOCUMENTS

EP    0980687 A2    2/2000
EP    1044374 B1    10/2008
(Continued)

OTHER PUBLICATIONS

Extended European Search Report Dated Apr. 4, 2013 for Related European Application.

(Continued)

*Primary Examiner* — Gerald Landry, II
(74) *Attorney, Agent, or Firm* — Dickinson Wright PLLC

(57) ABSTRACT

Provided is an extended use self-contained, wearable medical device. The device is preferably configured with an infusion deployment mechanism for variably inserting and retracting an infusion needle to different depths, or completely retracting the infusion needle from the infusion site and then re-inserting the infusion needle after a predetermined period of time, throughout an infusion cycle for extending the viability of the infusion site. Another embodiment comprises dual needle deployment mechanisms which may also variably insert and retract the infusion needles. A flow sensor is preferably provided for detecting the stoppage of flow through the infusion cannula and signaling the needle deployment mechanism to attempt infusion at a different depth or to deploy a second infusion needle. A re-fillable reservoir assembly is preferably provided for supplying a drug over the extended use of the device. Another embodiment comprises a partially reusable and partially disposable medical device implementing the above features.

17 Claims, 18 Drawing Sheets

(51) Int. Cl.
  *A61M 5/31* (2006.01)
  *A61M 5/14* (2006.01)
  *A61M 5/38* (2006.01)
  *A61M 5/46* (2006.01)
  *A61M 5/158* (2006.01)

(56) References Cited

U.S. PATENT DOCUMENTS

| | | | |
|---|---|---|---|
| 4,204,538 A | 5/1980 | Cannon | |
| 4,685,902 A | 8/1987 | Edwards et al. | |
| 4,723,947 A | 2/1988 | Konopka | |
| 4,734,092 A | 3/1988 | Millerd | |
| 4,755,173 A | 7/1988 | Konopka et al. | |
| 5,176,662 A | 1/1993 | Bartholomew et al. | |
| 5,226,899 A | 7/1993 | Lee et al. | |
| 5,242,406 A * | 9/1993 | Gross et al. | 604/132 |
| 5,257,980 A | 11/1993 | Van Antwerp et al. | |
| 5,453,099 A | 9/1995 | Lee et al. | |
| 5,496,284 A | 3/1996 | Waldenburg | |
| 5,522,803 A | 6/1996 | Teissen-Simony | |
| 5,536,249 A | 7/1996 | Castellano et al. | |
| 5,545,143 A | 8/1996 | Fischell | |
| 5,545,152 A | 8/1996 | Funderburk et al. | |
| 5,593,390 A | 1/1997 | Castellano et al. | |
| 5,728,074 A | 3/1998 | Castellano et al. | |
| 5,800,420 A * | 9/1998 | Gross et al. | 604/890.1 |
| 5,820,602 A | 10/1998 | Kovelman et al. | |
| 5,851,197 A | 12/1998 | Marano et al. | |
| 5,858,001 A | 1/1999 | Tsals et al. | |
| 5,858,005 A | 1/1999 | Kriesel | |
| 5,925,021 A | 7/1999 | Castellano et al. | |
| 5,957,895 A | 9/1999 | Sage et al. | |
| 5,968,011 A | 10/1999 | Larsen et al. | |
| 5,980,506 A | 11/1999 | Mathiasen | |
| 6,017,328 A | 1/2000 | Fischell et al. | |
| 6,056,718 A | 5/2000 | Funderburk et al. | |
| 6,068,615 A | 5/2000 | Brown et al. | |
| 6,074,369 A | 6/2000 | Sage et al. | |
| 6,086,575 A | 7/2000 | Mejslov | |
| 6,093,172 A | 7/2000 | Funderburk et al. | |
| 6,110,148 A | 8/2000 | Brown et al. | |
| 6,123,690 A | 9/2000 | Mejslov | |
| 6,132,400 A | 10/2000 | Waldenburg | |
| 6,175,752 B1 | 1/2001 | Say et al. | |
| 6,206,134 B1 * | 3/2001 | Stark et al. | 181/131 |
| 6,254,586 B1 | 7/2001 | Mann et al. | |
| 6,272,364 B1 | 8/2001 | Kurnik | |
| 6,275,717 B1 | 8/2001 | Gross et al. | |
| 6,277,627 B1 | 8/2001 | Hellinga | |
| 6,293,925 B1 | 9/2001 | Safabash et al. | |
| 6,302,866 B1 | 10/2001 | Marggi | |
| 6,352,523 B1 | 3/2002 | Brown et al. | |
| 6,355,021 B1 | 3/2002 | Nielsen et al. | |
| 6,391,005 B1 | 5/2002 | Lum et al. | |
| 6,485,461 B1 | 11/2002 | Mason et al. | |
| 6,520,938 B1 | 2/2003 | Funderburk et al. | |
| 6,521,446 B2 | 2/2003 | Hellinga | |
| 6,544,212 B2 | 4/2003 | Galley et al. | |
| 6,546,269 B1 | 4/2003 | Kurnik | |
| 6,551,276 B1 | 4/2003 | Mann et al. | |
| 6,558,351 B1 | 5/2003 | Steil et al. | |
| 6,565,509 B1 | 5/2003 | Say et al. | |
| 6,576,430 B1 | 6/2003 | Hsieh et al. | |
| 6,579,267 B2 | 6/2003 | Lynch et al. | |
| 6,589,229 B1 | 7/2003 | Connelly et al. | |
| 6,607,509 B2 | 8/2003 | Bobroff et al. | |
| 6,656,158 B2 | 12/2003 | Gregory et al. | |
| 6,656,159 B2 | 12/2003 | Flaherty | |
| 6,669,669 B2 | 12/2003 | Flaherty et al. | |
| 6,692,457 B2 | 2/2004 | Flaherty | |
| 6,699,218 B2 | 3/2004 | Flaherty et al. | |
| 6,706,159 B2 | 3/2004 | Moerman et al. | |
| 6,723,072 B2 | 4/2004 | Flaherty et al. | |
| 6,740,059 B2 | 5/2004 | Flaherty | |
| 6,749,560 B1 | 6/2004 | Konstrorum et al. | |
| 6,749,587 B2 | 6/2004 | Flaherty | |
| 6,768,425 B2 | 7/2004 | Flaherty et al. | |
| 6,830,558 B2 | 12/2004 | Flaherty et al. | |
| 6,830,562 B2 | 12/2004 | Mogensen et al. | |
| 6,840,922 B2 | 1/2005 | Nielsen et al. | |
| 6,852,104 B2 | 2/2005 | Blomquist | |
| 6,949,084 B2 | 9/2005 | Marggi et al. | |
| 6,960,162 B2 | 11/2005 | Saadat et al. | |
| 6,960,192 B1 | 11/2005 | Flaherty et al. | |
| 6,977,180 B2 | 12/2005 | Hellinga et al. | |
| 6,997,907 B2 | 2/2006 | Safabash et al. | |
| 7,004,928 B2 | 2/2006 | Aceti et al. | |
| 7,018,360 B2 | 3/2006 | Flaherty et al. | |
| 7,029,455 B2 | 4/2006 | Flaherty | |
| 7,052,251 B2 | 5/2006 | Nason et al. | |
| 7,064,103 B2 | 6/2006 | Pitner et al. | |
| 7,070,580 B2 | 7/2006 | Nielsen | |
| 7,083,597 B2 | 8/2006 | Lynch et al. | |
| 7,109,878 B2 | 9/2006 | Mann et al. | |
| 7,128,727 B2 | 10/2006 | Flaherty et al. | |
| 7,137,964 B2 | 11/2006 | Flaherty | |
| 7,144,384 B2 | 12/2006 | Gorman et al. | |
| 7,207,974 B2 | 4/2007 | Safabash et al. | |
| 7,214,207 B2 | 5/2007 | Lynch et al. | |
| 7,226,278 B2 | 6/2007 | Nason et al. | |
| 7,303,543 B1 | 12/2007 | Maule et al. | |
| 7,303,549 B2 | 12/2007 | Flaherty et al. | |
| 7,310,544 B2 | 12/2007 | Brister et al. | |
| 7,318,816 B2 | 1/2008 | Bobroff et al. | |
| 7,329,239 B2 | 2/2008 | Safabash et al. | |
| 7,354,420 B2 | 4/2008 | Steil et al. | |
| 7,496,392 B2 | 2/2009 | Alarcon et al. | |
| 7,722,595 B2 | 5/2010 | Pettis et al. | |
| 2002/0040208 A1 | 4/2002 | Flaherty et al. | |
| 2003/0055380 A1 | 3/2003 | Flaherty | |
| 2003/0109829 A1 | 6/2003 | Mogensen et al. | |
| 2003/0176852 A1 | 9/2003 | Lynch et al. | |
| 2003/0199823 A1 | 10/2003 | Bobroff et al. | |
| 2004/0002682 A1 | 1/2004 | Kovelman et al. | |
| 2004/0010207 A1 | 1/2004 | Flaherty et al. | |
| 2004/0059316 A1 | 3/2004 | Smedegaard | |
| 2004/0078028 A1 | 4/2004 | Flaherty et al. | |
| 2004/0092865 A1 | 5/2004 | Flaherty et al. | |
| 2004/0092878 A1 | 5/2004 | Flaherty | |
| 2004/0116847 A1 * | 6/2004 | Wall | A61K 9/0019 604/93.01 |
| 2004/0116866 A1 | 6/2004 | Gorman et al. | |
| 2004/0127844 A1 | 7/2004 | Flaherty | |
| 2004/0153032 A1 | 8/2004 | Garribotto et al. | |
| 2004/0162521 A1 * | 8/2004 | Bengtsson | 604/136 |
| 2004/0204673 A1 | 10/2004 | Flaherty | |
| 2004/0204687 A1 | 10/2004 | Mogensen et al. | |
| 2004/0220551 A1 | 11/2004 | Flaherty et al. | |
| 2004/0235446 A1 | 11/2004 | Flaherty et al. | |
| 2004/0260233 A1 | 12/2004 | Garibotto et al. | |
| 2005/0021005 A1 | 1/2005 | Flaherty et al. | |
| 2005/0022274 A1 | 1/2005 | Campbell et al. | |
| 2005/0043687 A1 | 2/2005 | Mogensen et al. | |
| 2005/0065760 A1 | 3/2005 | Murtfeldt et al. | |
| 2005/0090784 A1 | 4/2005 | Nielsen et al. | |
| 2005/0101932 A1 | 5/2005 | Cote et al. | |
| 2005/0101933 A1 | 5/2005 | Marrs et al. | |
| 2005/0113761 A1 | 5/2005 | Faust et al. | |
| 2005/0124936 A1 | 6/2005 | Mogensen et al. | |
| 2005/0171512 A1 | 8/2005 | Flaherty | |
| 2005/0182366 A1 | 8/2005 | Vogt et al. | |
| 2005/0203461 A1 * | 9/2005 | Flaherty et al. | 604/131 |
| 2005/0215982 A1 | 9/2005 | Malave et al. | |
| 2005/0222645 A1 | 10/2005 | Malave et al. | |
| 2005/0238507 A1 | 10/2005 | DiIanni et al. | |
| 2005/0245799 A1 | 11/2005 | Brauker et al. | |
| 2005/0273076 A1 | 12/2005 | Beasley et al. | |
| 2005/0283144 A1 | 12/2005 | Shiono et al. | |
| 2006/0041229 A1 | 2/2006 | Garibotto et al. | |
| 2006/0074381 A1 | 4/2006 | Malave et al. | |
| 2006/0122577 A1 | 6/2006 | Poulsen et al. | |
| 2006/0129090 A1 | 6/2006 | Moberg et al. | |
| 2006/0135913 A1 | 6/2006 | Ethelfeld | |
| 2006/0142698 A1 | 6/2006 | Ethelfeld | |

(56) References Cited

U.S. PATENT DOCUMENTS

| | | | |
|---|---|---|---|
| 2006/0178633 A1 | 8/2006 | Garibotto et al. | |
| 2006/0200073 A1* | 9/2006 | Radmer et al. | 604/93.01 |
| 2006/0263839 A1 | 11/2006 | Ward et al. | |
| 2006/0264835 A1 | 11/2006 | Nielsen et al. | |
| 2006/0282290 A1 | 12/2006 | Flaherty et al. | |
| 2007/0016149 A1 | 1/2007 | Hunn et al. | |
| 2007/0021733 A1 | 1/2007 | Hansen et al. | |
| 2007/0049865 A1 | 3/2007 | Radmer et al. | |
| 2007/0055181 A1* | 3/2007 | Deem | A61K 41/0028 601/2 |
| 2007/0060989 A1* | 3/2007 | Deem | A61B 18/1477 607/99 |
| 2007/0073229 A1 | 3/2007 | Gorman et al. | |
| 2007/0073559 A1 | 3/2007 | Stangel | |
| 2007/0088244 A1 | 4/2007 | Miller et al. | |
| 2007/0088271 A1 | 4/2007 | Richards | |
| 2007/0118405 A1 | 5/2007 | Campbell et al. | |
| 2007/0149925 A1* | 6/2007 | Edwards et al. | 604/141 |
| 2007/0191702 A1 | 8/2007 | Yodfat et al. | |
| 2008/0004515 A1 | 1/2008 | Jennewine | |
| 2008/0021395 A1* | 1/2008 | Yodfat et al. | 604/151 |
| 2008/0051697 A1 | 2/2008 | Mounce et al. | |
| 2008/0051698 A1 | 2/2008 | Mounce et al. | |
| 2008/0051709 A1 | 2/2008 | Mounce et al. | |
| 2008/0051710 A1 | 2/2008 | Moberg et al. | |
| 2008/0051711 A1 | 2/2008 | Mounce et al. | |
| 2008/0051714 A1 | 2/2008 | Moberg et al. | |
| 2008/0051716 A1 | 2/2008 | Stutz | |
| 2008/0051718 A1 | 2/2008 | Kavazov et al. | |
| 2008/0051727 A1 | 2/2008 | Moberg et al. | |
| 2008/0051730 A1 | 2/2008 | Bikovsky | |
| 2008/0051738 A1 | 2/2008 | Griffin | |
| 2008/0051765 A1 | 2/2008 | Mounce | |
| 2008/0097321 A1 | 4/2008 | Mounce et al. | |
| 2008/0097326 A1 | 4/2008 | Moberg et al. | |
| 2008/0097327 A1 | 4/2008 | Bente et al. | |
| 2008/0097328 A1 | 4/2008 | Moberg et al. | |
| 2008/0097375 A1 | 4/2008 | Bikovsky | |
| 2008/0097381 A1 | 4/2008 | Moberg et al. | |
| 2008/0116647 A1 | 5/2008 | Anderson et al. | |
| 2008/0119707 A1* | 5/2008 | Stafford | 600/365 |
| 2008/0132842 A1 | 6/2008 | Flaherty | |
| 2008/0147041 A1 | 6/2008 | Kristensen | |
| 2008/0160492 A1 | 7/2008 | Campbell et al. | |
| 2008/0194924 A1 | 8/2008 | Valk et al. | |
| 2008/0215006 A1 | 9/2008 | Thorkild | |
| 2008/0261255 A1 | 10/2008 | Tolosa et al. | |
| 2008/0264261 A1 | 10/2008 | Kavazov et al. | |
| 2008/0269680 A1 | 10/2008 | Ibranyan et al. | |
| 2008/0269713 A1 | 10/2008 | Kavazov | |
| 2008/0281297 A1* | 11/2008 | Pesach et al. | 604/890.1 |
| 2008/0294028 A1 | 11/2008 | Brown | |
| 2008/0306434 A1 | 12/2008 | Dobbles et al. | |
| 2008/0312608 A1 | 12/2008 | Christoffersen et al. | |
| 2009/0005724 A1 | 1/2009 | Regittnig et al. | |
| 2009/0005728 A1 | 1/2009 | Weinert et al. | |
| 2009/0012472 A1 | 1/2009 | Ahm et al. | |
| 2009/0062767 A1* | 3/2009 | Van Antwerp et al. | 604/504 |
| 2009/0076453 A1 | 3/2009 | Mejlhede et al. | |
| 2009/0149830 A1* | 6/2009 | Spector | A61H 39/08 604/506 |
| 2009/0204077 A1 | 8/2009 | Hasted et al. | |
| 2009/0221971 A1 | 9/2009 | Mejlhede et al. | |
| 2009/0281497 A1* | 11/2009 | Kamen et al. | 604/151 |
| 2011/0054400 A1 | 3/2011 | Chong et al. | |

FOREIGN PATENT DOCUMENTS

| | | | |
|---|---|---|---|
| JP | 2004524869 A | 8/2004 | |
| WO | 0185233 A2 | 11/2001 | |
| WO | 03074121 A1 | 9/2003 | |
| WO | WO2007051139 | 5/2007 | |
| WO | 2009001345 A1 | 12/2008 | |
| WO | 2009004627 A2 | 1/2009 | |
| WO | 2009016636 A2 | 2/2009 | |
| WO | WO2009021039 | 2/2009 | |
| WO | WO2009021052 | 2/2009 | |
| WO | 2009044401 A2 | 9/2009 | |

OTHER PUBLICATIONS

Japanese Official Notice of Final Decision of Rejection dated Feb. 17, 2015.
Chinese Office Action Dated Feb. 5, 2013 Issued on Related Chinese Application, and English Translation Thereof.

* cited by examiner

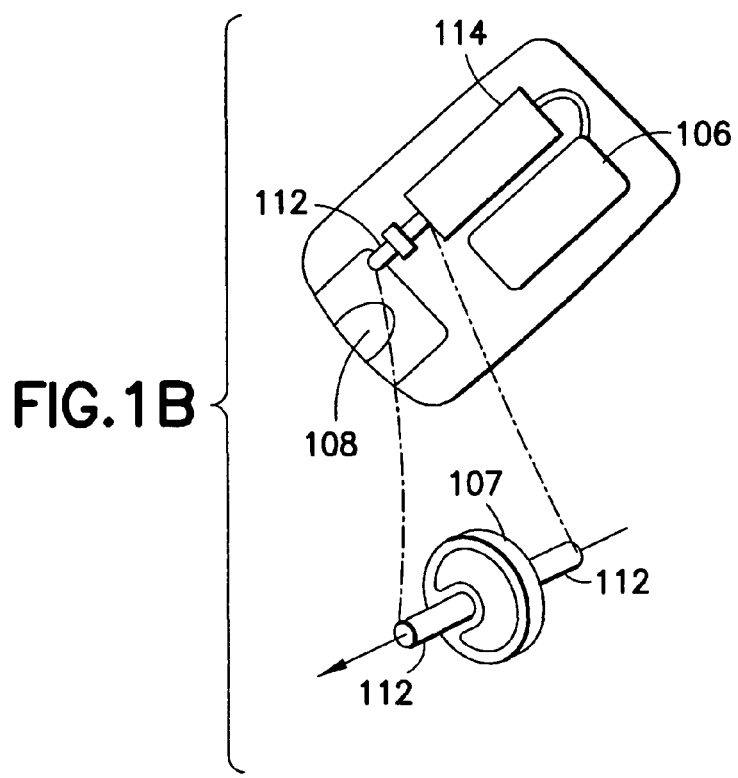
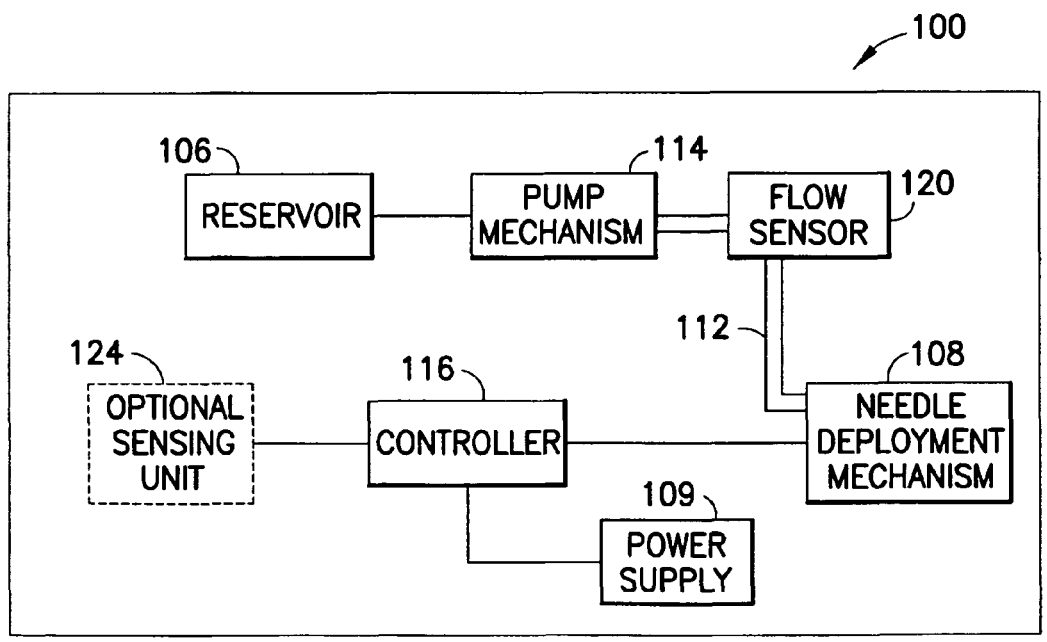

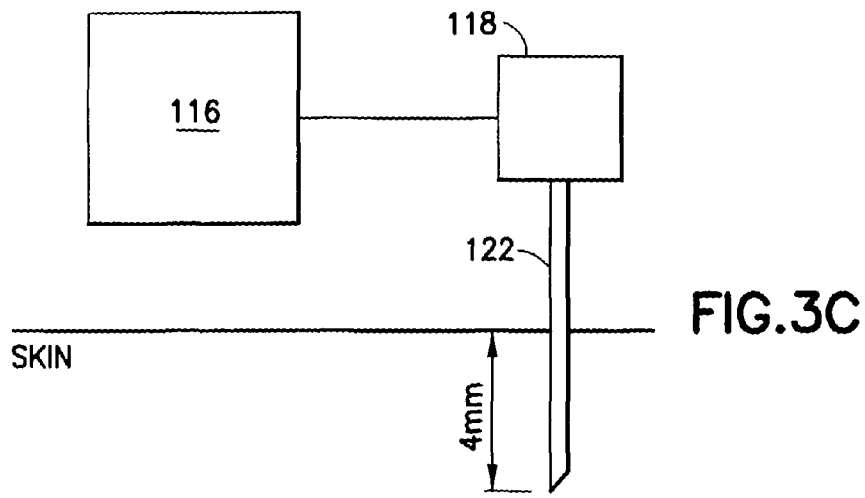
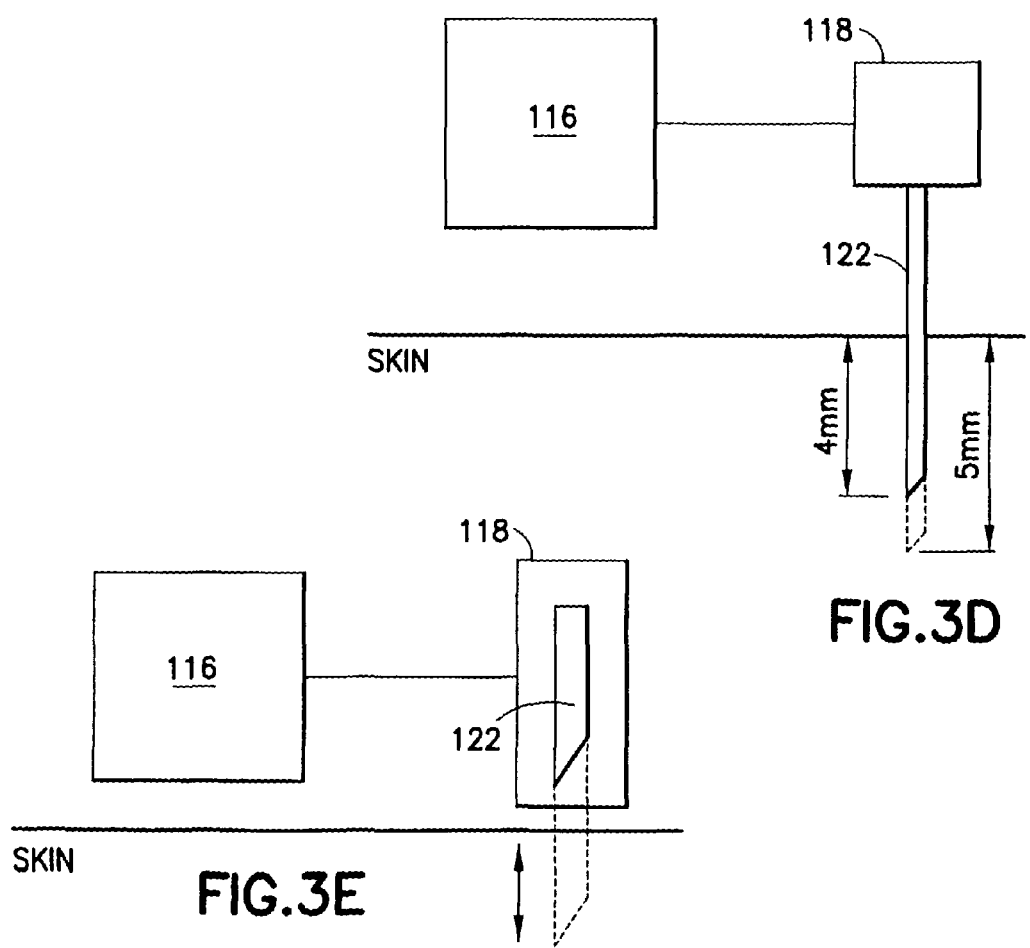

EXTENDED USE MEDICAL DEVICE

FIELD OF THE INVENTION

The present invention relates generally to wearable, self-contained drug infusion devices providing lower cost of therapy and an extended period of use by prolonging viability of the infusion site. Additionally, the extended use drug infusion device is enabled to effectively provide continuous glucose monitoring previously unavailable to common wearable drug infusion devices. An additional embodiment provides a programmable drug delivery device for use in conjunction with the drug infusion devices above, for providing even further control and precision of drug therapy.

BACKGROUND OF THE INVENTION

Diabetes is a group of diseases marked by high levels of blood glucose resulting from defects in insulin production, insulin action, or both. There are 23.6 million people in the United States, or 8% of the population, who have diabetes. The total prevalence of diabetes has increased 13.5% since the 2005-2007 time period. Diabetes can lead to serious complications and premature death, but there are well-known products available for people with diabetes to help control the disease and lower the risk of complications.

Treatment options for people with diabetes include specialized diets, oral medications and/or insulin therapy. The primary goal for diabetes treatment is to control the patient's blood glucose (sugar) level in order to increase the chances of a complication-free life. It is not always easy, however, to achieve good diabetes management, while balancing other life demands and circumstances.

Currently, there are two principal modes of daily insulin therapy for the treatment of type 1 diabetes. The first mode includes syringes and insulin pens that require a needle stick at each injection, typically three to four times per day, but are simple to use and relatively low in cost. Another widely adopted and effective method of treatment for managing diabetes is the use of a conventional insulin pump. Insulin pumps can help the user keep their blood glucose levels within target ranges based on their individual needs, by continuous controlled infusion of insulin. By using an insulin pump, the user can match their insulin therapy to their lifestyle, rather than matching their lifestyle to how an insulin injection, for example, is working for them.

Conventional insulin pumps are capable of delivering rapid or short-acting insulin 24 hours a day through a catheter placed under the skin. Insulin doses are typically administered at a basal rate and in a bolus dose. Basal insulin is delivered continuously over 24 hours, with the goal of keeping one's blood glucose levels in a consistent range between meals and overnight. Some insulin pumps are capable of programming the basal rate of insulin to vary according to the different times of the day and night. Bolus doses are typically administered when the user takes a meal, and generally provide a single additional insulin injection to balance the carbohydrates consumed. Some conventional insulin pumps enable the user to program the volume of the bolus dose in accordance with the size or type of the meal consumed. Conventional insulin pumps also enable a user to take in a correctional or supplemental bolus of insulin to compensate for a low blood glucose level at the time the user is calculating a meal bolus.

There are many advantages of conventional insulin pumps over other methods of diabetes treatment. Insulin pumps deliver insulin over time rather than in single injections and thus typically result in less variation within the blood glucose range that is recommended by the American Diabetes Association (ADA). Conventional insulin pumps reduce the number of needle sticks which the patient must endure, and make diabetes management easier and more effective for the user, thus considerably enhancing the quality of the user's life. Insulin pumps however can be cumbersome to use and are typically more expensive than other methods of treatment. From a lifestyle standpoint, the conventional pump, tubing, and infusion set may be inconvenient and bothersome for the user.

New advances in insulin therapy provide "wearable" drug infusion devices that are lower in cost and more convenient and comfortable to use than conventional insulin pumps. Some of these devices are intended to be partially or entirely disposable, and in theory provide many of the advantages of conventional insulin pumps without the initial high cost and inconvenience of conventional insulin pumps.

Wearable medical devices capable of performing similar functions as conventional insulin pumps are becoming increasingly more prevalent, but are still high in cost. While the initial cost of each wearable medical device is much lower than conventional insulin pumps, the cost for providing drug therapy over an entire year using the wearable medical devices is magnified due to the short duration of use of such medical devices. Common wearable medical devices are typically disposed of after a maximum of 3 days in operation. Some driving factors for the duration of use for such medical devices include the viability of the infusion site for a prolonged period and the challenges of reasonably providing an adequate supply of insulin over such a prolonged period, as well as efficiently providing a durable power source over the extended life of the device. Extending the use of a wearable medical device to last from 5-7 days would greatly reduce the daily cost of therapy, thus enabling a larger population to afford the conveniences provided by such therapy. Therefore, the availability of such wearable medical devices may be increased if the daily cost of such therapy were reduced.

Accordingly, there is a need in the art for extending the duration of use of wearable medical devices, thus providing more cost-effective drug therapy, so that many more diabetes patients can benefit from the advantages these devices provide.

Additionally, most wearable medical devices available in the art are typically referred to as either "smart" or "simple" medical devices. "Smart" patch pumps commonly available in the art typically receive instructions from and/or transmit patient data to an intelligent controller or host device, which requires either wireless or tethered communication between the pump and controller. "Smart" patch pumps are typically larger in size than "simple" patch pumps, heavier and more expensive due to the additional components necessary for providing communication with the host device. Additionally, typical "smart" devices require user interaction for blood glucose monitoring, bolus calculation, and dose programming, which add complexity and risk to the intended use of these devices. "Simple" patch pumps commonly available, on the other hand, typically provide only a preset basal dose. For many users, the level of complexity for a "smart" device is unacceptable, but their therapeutic requirements cannot be satisfied with a "simple" patch pump. Therefore, there is a need for providing specialized insulin therapy, not available from a "simple" patch pump, without the added cost and complexity of a "smart" patch pump.

SUMMARY OF THE INVENTION

Exemplary embodiments of the present invention address at least the above problems and/or disadvantages and provide at least the advantages described below. Accordingly, it is an object of certain embodiments of the present invention to provide a wearable medical device that further reduces the daily cost of insulin therapy by extending the duration of use of the medical device. Another object of certain embodiments of the present invention is to provide a pre-programmable patch pump that provides specialized insulin therapy without the high cost typically associated with "smart" patch pumps.

A first aspect of the present invention provides a medical device for administering drug therapy to a user over an extended period of use. The medical device comprises a pump mechanism for administering a drug to the user, first and second delivery cannulas for infusing said drug transdermally into the user at first and second infusion sites, and first and second mechanisms for separately controlling deployment of the first and second cannulas into said user at said first and second infusion sites. The medical device further comprises a flow sensing unit for detecting whether the first infusion site is no longer viable by sensing whether the first delivery cannula is blocked or otherwise incapable of delivering a desired flow of drug to the user wherein the first delivery cannula is retracted from the user when the flow sensing unit detects that the infusion site is no longer viable. Additionally, the first delivery cannula may be retracted from the user after a predetermined period of use. The second delivery cannula is deployed into the user when the first delivery cannula is retracted, wherein the first and second mechanisms for controlling deployment of the first and second delivery cannulas are manually or automatically actuated. The medical device further comprises a reservoir for supplying a volume of drug necessary for the extended duration of use of the medical device. The medical device may further comprise a first and second reservoir for supplying the drug to the respective first and second delivery cannulas. The medical device may also comprise a refillable reservoir for supplying the drug infused into the user, said reservoir including a port or septum for receiving a supply of the drug, or may even comprise a receptacle for receiving a pre-filled reservoir assembly. Additionally, the medical device may comprise a reusable and disposable portion, wherein the pump mechanism and the first and second mechanisms for controlling deployment of the first and second cannulas are housed in the reusable portion of the medical device.

A second aspect of the present invention provides a medical device for administering drug therapy to a user over an extended period of use. The medical device comprises a pump mechanism for administering a drug to the user, a delivery cannula for infusing said drug transdermally into the user at an infusion site, and a mechanism for controlling deployment of the cannula into said user, wherein said mechanism is configured to variably move said cannula to a first depth and a second depth throughout the duration of use of the medical device. The mechanism for controlling deployment of said cannula is configured to retract said cannula after a predetermined period of use and further re-deploy said cannula into said user after a predetermined period of non-use. The medical device also comprises a disposable and reusable portion wherein the pump mechanism and mechanism for controlling deployment of the cannula are contained in the reusable portion of the medical device.

A third aspect of the present invention extends the use of a medical device comprising a first and second delivery cannula for administering drug therapy to a user by deploying the first cannula into the user at an infusion site for administering a drug to the user, retracting said first cannula from said user, and deploying the second cannula into said user at a second infusion site for administering said drug to said user. The method also determines whether the infusion site is no longer viable by detecting that the first cannula is blocked or is incapable of delivering a desired flow of drug to the user and retracts said first cannula from said user when it is determined that the infusion site is no longer viable. The method may also retract said first cannula from said user after a predetermined period of use. The steps of deploying further comprise automatically or manually deploying the respective cannulas into the user at the respective infusion sites.

A fourth aspect of the present invention extends the use of a medical device comprising a single delivery cannula for administering drug therapy to a user by deploying the delivery cannula into the user at an infusion site to a desired depth for administering a drug to said user, and variably moving said cannula to a second desired depth, while administering said drug to said user. The method further determines whether a flow of the drug to said user is inhibited and variably moves said cannula to said second desired depth when it is determined that the flow of the drug is inhibited. The method may also variably move said cannula to said second desired depth after a predetermined period of use.

A fifth aspect of the present invention extends the use of a medical device comprising a single delivery cannula for administering drug therapy to a user by deploying the delivery cannula into the user at an infusion site to a desired depth for administering a drug to said user, determining a predetermined period of time has lapsed since deployment of said delivery cannula, retracting said cannula from the user when it is determined that the predetermined time has lapsed, and re-inserting the cannula at the infusion site, after a second predetermined period, for re-administering the drug to said user. The method further re-inserts the cannula to a second desired depth.

Another aspect of the present invention provides a partially disposable and partially reusable medical device for administering drug therapy to a user. The medical device comprises a reusable housing and a disposable housing, each with at least one exposed interface for engaging each other. The reusable housing contains a pump mechanism for administering a drug to the user, a cannula deployment mechanism for deploying a delivery cannula for infusing said drug into the user, and controller for controlling the pump mechanism and the cannula deployment mechanism. The disposable housing contains the delivery cannula and a reservoir for housing a drug supply for infusion into said user. The reusable housing may further contain a sensor deployment mechanism.

Yet another aspect of the present invention provides a drug delivery device with a programmable controller, a drug cartridge, an infusion needle, and a micro-pump provided between the infusion needle and the drug cartridge, wherein the controller is programmed by a host device which calculates a bolus dose of a drug to be administered to the user through said infusion needle and programs the controller to set said dosage to be administered to the user. The drug delivery device is preferably an insulin pen and the host device is one of a personal diabetes manager, a blood glucose monitor, a bolus calculator and a wearable drug infusion device of one of the exemplary embodiments of the present invention. The host device preferably calculates the bolus dosage from at least one factor selected from the list consisting of a test strip result, bodily function sensor signal, basal rate infusion history, and meal information. The programmable drug delivery device preferably comprises an electrical contact for directly communicating with the host device and may alternatively communicate to the host device via a personal area network. The programmable delivery device is preferably programmed when in direct communication with the host device and also comprises a rechargeable battery that is recharged when in direct contact to the host device.

A final aspect of the present invention provides a wearable medical device for administering drug therapy to a user comprising an integral housing containing a reservoir for housing a supply of a drug, in fluid communication with an infusion cannula for delivering the drug to the user, a pump mechanism device for administering delivery of the drug from the reservoir to the user through the infusion cannula, and a preprogrammed controller to control the pump mechanism to provide a preprogrammed drug delivery profile to the user. The controller is preferably pre-programmed by either a manufacturer of the medical device or a health care provider and may be pre-programmed to provide a specific drug infusion rate according to an electronic timer or the time of day or alternately may be pre-programmed to provide multiple daily infusions of a dosage of drug to the user.

Objects, advantages and salient features of the invention will become apparent to those skilled in the art from the following detailed description, which, taken in conjunction with annexed drawings, discloses exemplary embodiments of the invention.

BRIEF DESCRIPTION OF THE DRAWINGS

The above and other exemplary features and advantages of certain exemplary embodiments of the present invention will become more apparent from the following description of certain exemplary embodiments thereof when taken in conjunction with the accompanying drawings, in which:

FIG. 1B is an illustration of a priming mechanism for use in a medical device according to an exemplary embodiment of the present invention;

FIG. 2 is a block diagram depicting the principal components of the medical device according to an embodiment of the present invention;

FIGS. 3C-3E illustrate exemplary operations of a needle deployment mechanism according to exemplary embodiments of the present invention;

Throughout the drawings, like reference numerals will be understood to refer to like elements, features and structures.

DETAILED DESCRIPTION OF EXEMPLARY EMBODIMENTS

The matters exemplified in this description are provided to assist in a comprehensive understanding of exemplary embodiments of the invention, and are made with reference to the accompanying figures. Accordingly, those of ordinary skill in the art will recognize that various changes and modifications of the exemplary embodiments described herein can be made without departing from the scope and spirit of the claimed invention. Also, descriptions of well-known functions and constructions are omitted for clarity and conciseness.

Figure 1A:
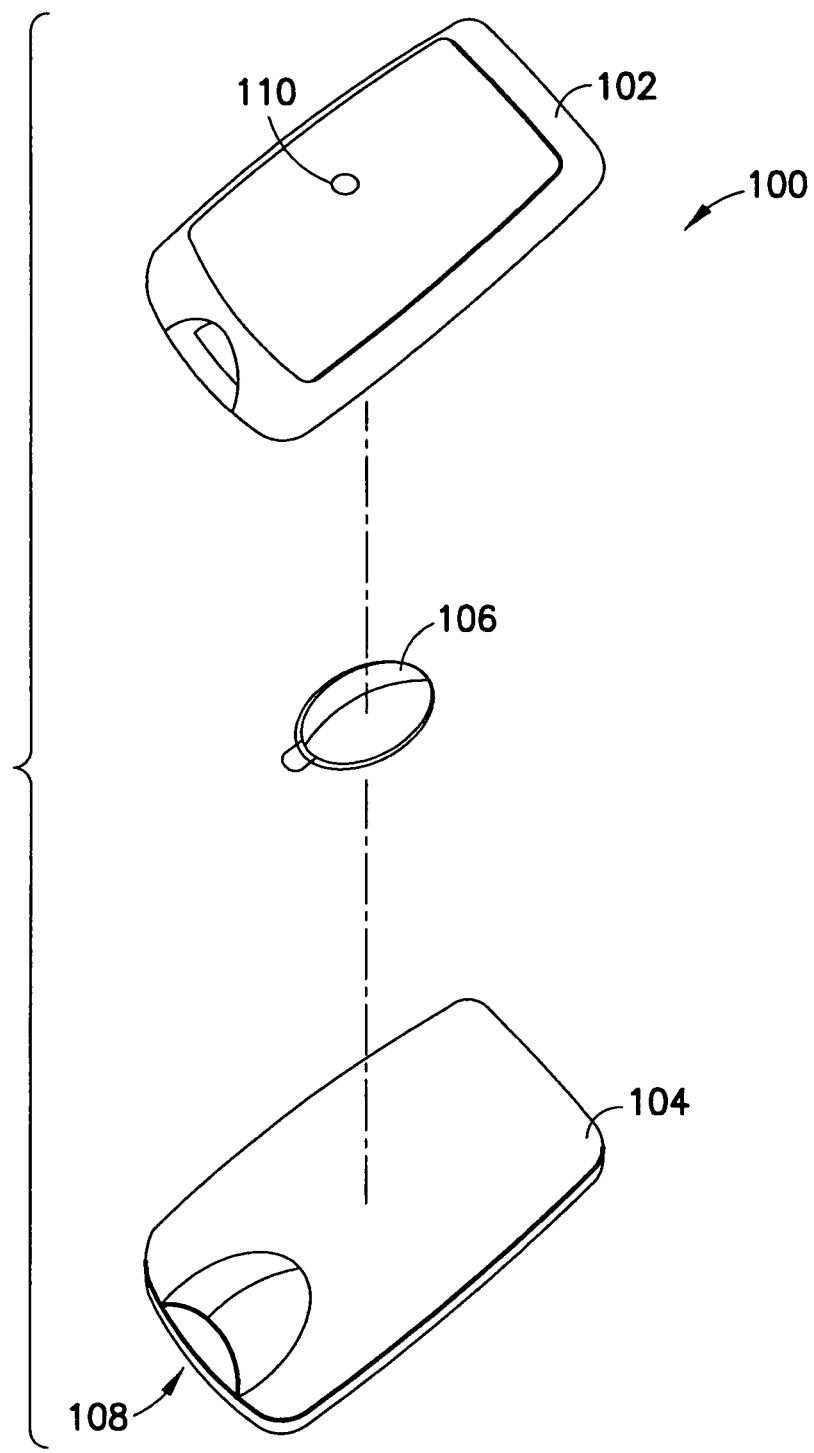
FIG. 1A is an illustration depicting a medical device according to an exemplary embodiment of the present invention.

A general embodiment of medical device 100 is illustrated in FIGS. 1 and 2. Medical device 100 is preferably a wearable medical device provided for the delivery of a liquid or gel medication, preferably but not necessarily insulin, by continuous infusion into or through the skin of the patient. Such known medical devices are commonly referred to as "patch pumps" due to their nature of being worn or affixed to the user's skin. Medical device 100 generally comprises a housing, shown in FIG. 1A as comprising an upper housing portion 102 and a lower housing portion 104, a rigid or flexible drug reservoir 106 or other container for supplying a medication, an infusion needle mechanism 108 and a pump mechanism 114 for controlling the delivery of the drug through the flow channel 112 into the user's body through an infusion needle provided in the infusion needle mechanism 108. Medical device 100 also preferably comprises a microprocessor or controller 116 for directing the infusion needle mechanism and pump mechanism as well as monitoring and/or controlling other preferred operations and systems of the medical device 100. Medical device 100 may also comprise an optional flow sensor 120 and optional power supply 109, such as any known power source including, but not limited to, a standard battery, capacitor, or energy harvesting system such as that disclosed in co-assigned and co-pending U.S. patent application Ser. No. 12/458,807, filed Jul. 23, 2009, which is incorporated herein by reference.

One exemplary embodiment of medical device 100 is a pre-programmed patch pump. Pre-programmed patch pumps may comprise simple intelligence for providing a customized basal infusion rate that can be varied throughout the day to match sleeping and waking insulin requirements. The pre-programmed patch pump can be programmed to deliver a drug or drugs to the user at different rates for different times of day or under different conditions. Varying drug delivery rates over time are referred to herein as a drug delivery profile. The pre-programmed patch pump can be programmed either by the manufacturing facility or a health care provider and preferably requires no additional user programming. A pre-programmed patch pump may even be configured to provide multiple daily infusions and may be designed with a mechanism to enable manual actuation of an incremental bolus dose. One form of manual actuation would require the closure of an electrical contact, such as a momentary switch or two momentary switches, for an extended duration, after which a vibratory or audible signal may confirm completion of drug delivery. The pre-programmed patch pump for use in exemplary embodiments of the present invention comprises enough intelligence to perform sensing of blockage of insulin flow, a low-level of insulin in the reservoir and other fault conditions. A pre-programmed patch pump also preferably provides alarms to the user in each of these fault conditions. Pre-programmed patch pumps perform similar functions as a "smart" patch pump except for communication with a host device, thus greatly reducing the cost of providing drug therapy with such a device and enhancing the ease of use for such a device. Exemplary embodiments of medical device 100 in the present invention are preferably directed to a pre-programmable patch pump, as discussed above.

Medical device 100, in other embodiments of the present invention, may also be provided as a fully-programmable ("smart"), or ("simple") package, as would be appreciated by one of ordinary skill in the art. A fully programmable package provides the user with the greatest precision and flexibility in controlling the rate of administering a drug that is suitable for the user's lifestyle, but does require additional cost. Fully-programmable "smart" patch pumps are generally used in conjunction with a Blood Glucose Monitor (BGM) or Continuous Glucose Monitor (CGM) and a host device, such as a Personal Diabetes Monitor (PDM), to provide, through closed-loop control and sensing, a personalized basal infusion rate and bolus injections that may be activated or adjusted at any time throughout the day. "Smart" patch pumps are preferably configured to be in communication with the host device, such as via a personal area network as described in previously incorporated, co-pending U.S. application Ser. No. 12/458,807, or wireless network. "Smart" patch pumps may even communicate, continuously or intermittently, with the host device via a wired or other direct connection. "Simple" patch pumps can be provided with minimal or no system intelligence and generally comprise mostly mechanical systems for providing basic control of insulin infusion through either a preset basal rate or manually activated bolus injections. Each patch pump is particularly effective and desired for a certain type of user. A user's lifestyle, medical condition, financial situation and aptitude for operating a medical device largely determine which package of patch pump is suitable for that user. The specific features and functionality of exemplary embodiments of the present invention, to follow, may be implemented in each of the patch pump packages described above.

Additional embodiments, features and specific functionality of patch pumps to be used in accordance with the present invention can be found in commonly assigned U.S. Pat. No. 6,589,229 issued to Robert I Connelly, et al., co-pending and commonly assigned U.S. patent application Ser. No. 12/458, 807, and co-pending and commonly assigned U.S. patent application titled "Flexible and Conformal Patch Pump" filed on even date herewith (attorney docket number P-8678 (55581)), which are expressly incorporated herein by reference. One specific feature that may be provided in a medical device 100 as illustrated in FIG. 1B, is directed to an automatic or semi-automatic priming of the medical device prior to use. A drug flow channel 112 provided internal to medical device 100 begins at a drug reservoir 106 and terminates at an infusion needle inserted by an infusion needle deployment mechanism 108. In this embodiment, a hydrophobic membrane 107 in the shape of a disk is placed in the flow channel 112 near the infusion needle deployment mechanism 108. The hydrophobic membrane 107 allows any air trapped in the void volume of flow channel 112 to be purged from the flow channel when the pumping mechanism 114 is initially activated. The flow of fluid in flow channel 112 will drive the air from the flow channel 112 through hydrophobic membrane 107, which inhibits the flow of fluid from the flow channel 112 due to the specific membrane material, as well as the size, distribution and density of the pores in the membrane. The use of hydrophobic membrane 107 in an exemplary medical device is particularly effective since minimal back pressure is required for infusion. The specific distribution, density and size of the pores in an exemplary hydrophobic membrane may be chosen based on a particular drug or fluid to be provided through the flow channel, as well as other performance requirements. The cessation of fluid flow in the flow channel 112 can be sensed and communicated to the user, allowing the user to complete a start-up procedure and begin use of the medical device.

A first exemplary embodiment of medical device 100, constructed in accordance with the present invention is illustrated in FIG. 3C. As discussed above, one of the primary challenges in extending the duration of use of common patch pumps, is maintaining the viability of the infusion site over the extended period. The infusion site may be defined as the site where the infusion needle enters a user's skin. Maintaining a viable infusion site longer than 3 days is difficult since insulin can crystallize in the infusion needle, thus blocking the flow of insulin to the patient. Additionally, the user's body may react adversely in response to a foreign object in the body. The tissue at the infusion site may become inflamed over time causing increased resistance to infusion. Cell growth may occur on the infusion needle and local scarring is likely if the infusion needle remains inserted into the tissue. The first exemplary embodiment of the present invention preserves the viability of the infusion site by advancing or retracting an infusion needle 122 to varying depths in the user's skin throughout the infusion cycle. By adjusting the depth of infusion over the infusion cycle, the risk of inflammation and scarring at the infusion site and its associated complications can be reduced or avoided.

Figure 3A:
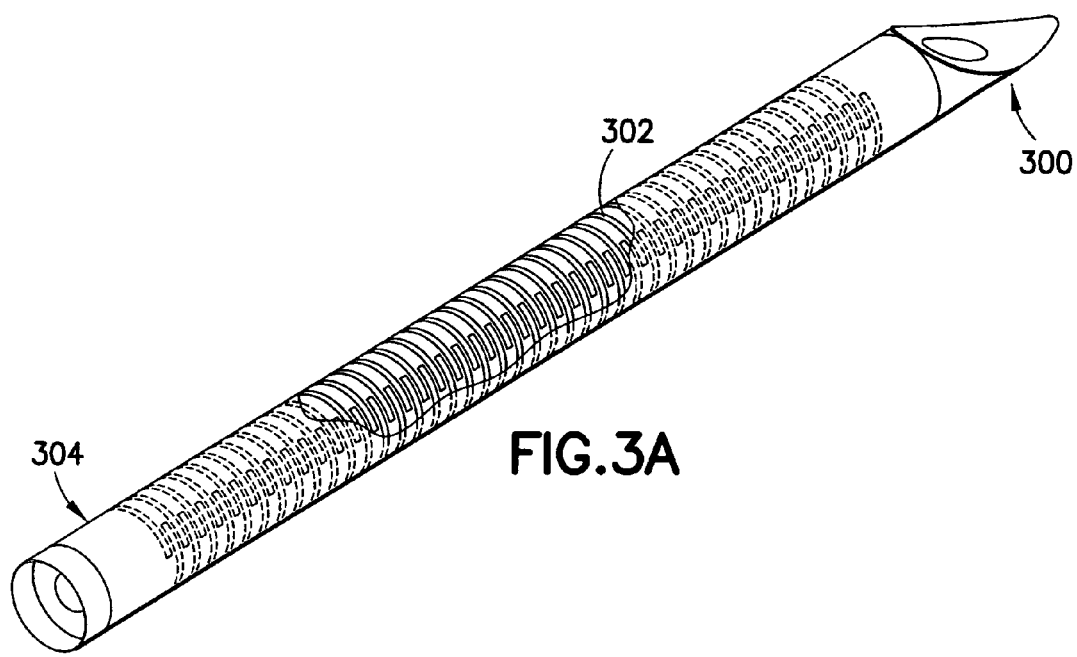
FIGS. 3A-3B illustrate exemplary infusion needles for use in a medical device according to an embodiment of the present invention.
Figure 3B:
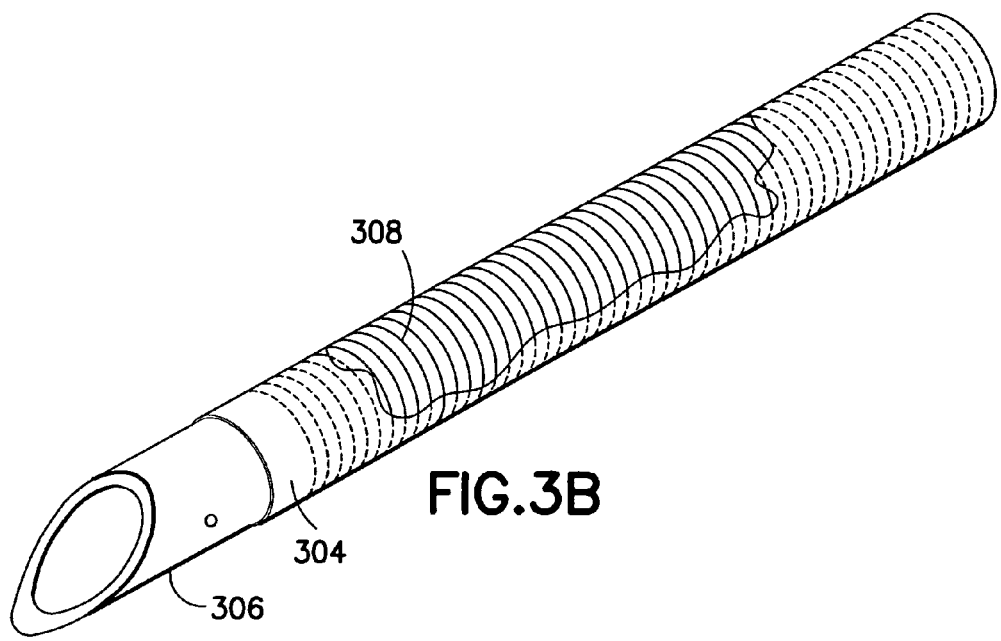

The infusion needle 122 for use in the exemplary embodiments of the present invention, is preferably flexible for enabling prolonged use and comfort for the user, yet maintains a suitable column strength that enables the infusion needle to be inserted into the user. One exemplary embodiment, as shown in FIG. 3A preferably comprises a stainless steel cannula 300 with a sharpened tip and alternating slots 302, laser cut or chemically etched, along the shaft of the cannula. The alternating slots 302 enable the cannula to flex, yet provide a rigidity or column strength necessary for insertion into the user's skin. The stainless steel cannula 300 is preferably a unitary body having a sharpened tip at the distal end. Cannula 300 is preferably sheathed or coated by a Vialon® or Teflon® sleeve 304 that provides a biocompatible outer fluid seal for enabling a drug fluid to enter to the user through the tip of the cannula. Additional disclosure of the exemplary Vialon® material can be found in commonly assigned U.S. Pat. Nos. 5,226,899 and 5,453,099 to Min-Shiu Lee et al., and U.S. Pat. No. 5,545,708 to Theo Onwunaka et al., each expressly incorporated herein by reference. Of course any suitable fluid tight material could be used to form the sheath or coat. Another exemplary embodiment of a flexible infusion needle 122 is shown in FIG. 3B. The exemplary embodiment in FIG. 3B preferably includes a sharpened stainless steel needle tip 306 attached to a torsion spring 308. Needle tip 306 enables penetration into the user's skin and is preferably welded to torsion spring 308 but may be attached using any suitable method. Torsion spring 308 provides similar benefits as the embodiment discussed in FIG. 3A and similarly also comprises a Vialon® or Teflon® sleeve 304 for sealing the fluid within the inner cavity of the torsion spring. Torsion spring 308 and stainless steel cannula 300 may be provided with any suitable cross section, and may alternatively comprise a rectangular cross-section to maximize the internal diameter, as would be appreciated by one of ordinary skill in the art. Additionally, the tips of the infusion needles shown in FIGS. 3A and 3B, do not need to comprise an opening for the flow of drug to the user. It may desirable to implement an infusion needle with a closed end, having side ports located near the tip for enabling the flow of drug to the user.

Infusion needle 122 for use in other exemplary embodiments may alternatively comprise a flexible cannula with a sharpened tip optionally hardened relative to the cannula shaft for entering the user's skin, a flexible cannula inserted with the aid of a rigid insertion needle or any other suitable device. The infusion needle deployment mechanism 108 shown in FIG. 1A may comprise a manual or automatic mechanism for inserting and retracting the infusion needle 122 into the user's skin. Additionally, needle deployment mechanism 108 may be either manually or automatically actuated to insert the infusion needle into the user's skin. Controller 116 may automatically actuate needle deployment mechanism 108 after initialization of the medical device or based on some other programmed or sensed condition. Further, automatic deployment may be effected via an appropriate command received from a BGM, PDM or a host device.

As shown in FIG. 3C, needle deployment mechanism 108 comprises a driver 118 for actuating the insertion and retraction of infusion needle 122. An exemplary mechanism of driver 118 suitable for use in the present invention provides a motor electronically controlled by controller 116 to drive the infusion needle 122 in an insertion and retraction direction by rotating a threaded rod in either a clockwise or counterclockwise motion, wherein the infusion needle moves axially along the threaded rod via a reciprocal threaded structure or sleeve. An alternative embodiment implements shape memory alloys and/or piezoelectric actuators, that contract when applied with an electric charge. Controller 116 can apply a variable voltage to the shape memory alloy or piezoelectric actuator to realize a desired distance of motion in either the insertion or retraction direction, to drive the infusion needle 122. Other embodiments of driver 118 suitable for use in the present invention may comprise multiple mechanically or electronically actuated latches, and/or springs for realizing motion of the infusion needle in the insertion and retraction direction, as is available to one of ordinary skill in the art. Driver 118 is preferably electronically controlled by controller 116, however, in certain embodiments driver 118 may be controlled by at least one of a thumb-wheel or mechanical dial, or by actuating push buttons, slide latches or levers. The driver 118 for use in the present invention is not limited to the above embodiments. One of ordinary skill in the art would recognize that any known mechanism capable of inserting and retracting a needle into a user may be suitable for use in an embodiment of the present invention such as the embodiments disclosed in U.S. Pat. No. 6,391,005 to Lum et al. and US Patent Publication 2004/0010207 to J. Christopher Flaherty et al., each expressly incorporated herein by reference.

In an exemplary embodiment of the present invention, illustrated in FIGS. 3D and 3E, infusion needle 122 is manually or automatically inserted to a desired depth into the user's skin, for example 4 mm, using any suitable method discussed above. Medical device 100 then commences drug infusion or injection into the user. After a predetermined period of time has lapsed, such as 1 or 2 days, controller 116 instructs driver 118 to further advance infusion needle 122 to a second depth of 5 mm, for example. By providing a second infusion depth, the infusion needle 122 can effectively infuse the drug into potentially uninflamed tissue, thus prolonging the duration of use of the infusion site. The above operation repeats if desired or necessary. Thus, after a second predetermined period of time has lapsed, controller 116 further instructs driver 118 to advance infusion needle 122 to a third infusion depth. In another exemplary embodiment, driver 118 initially inserts infusion needle 122 to a depth of 5 mm and after a predetermined period of time has lapsed, controller 116 instructs driver 118 to retract infusion needle 122 to a second, shallower infusion depth. One of ordinary skill in the art would recognize that any of the above embodiments may be combined in the present invention. For instance, controller 116 may variably control the infusion depth by instructing driver 118 to insert infusion needle 122 to a desired depth, retract the needle after a first period and then drive the needle to the original infusion depth or an alternative infusion depth after a second period. Driver 118 may be configured to effect any number of changes in infusion depth. Alternatively, driver 118 may be configured to provide only a single change in depth as may be easily performed using purely mechanical structures, perhaps for use in a simple patch pump.

In another exemplary embodiment, as can be seen in FIG. 3C, after initial insertion of infusion needle 122 and commencement of drug infusion, driver 118 can be controlled to completely or near completely withdraw infusion needle 122 from the infusion site for a predetermined period of time. In one embodiment, driver 118 may be actuated to withdraw infusion needle 122 from the user for up to 8 hours while the user is asleep and then re-insert or drive infusion needle 122 to a desired depth when the user wakes. Not only would this embodiment increase the viability of the infusion site by reducing the risk of inflammation at the infusion site, but it may also reduce tissue scarring of the patient.

Each of FIGS. 3C-3E illustrate driver 108 driving the infusion needle 122 in a direction perpendicular to the user's skin. In other embodiments, it is preferable that the infusion needle may be variably inserted and retracted into the user at an angle. By inserting infusion needle 122 into the user at an angle, the infusion needle passes through a greater amount of skin without penetrating to a greater depth. In view of the above embodiments, this may enable an increased distance between the infusion depths, thus providing an even increased duration of viability of the infusion site and improved comfort for the user.

Medical device 100 for use in the above embodiments may also include a flow sensor 120, as shown in FIG. 2, for detecting a flow rate of a drug provided by pump mechanism 114. Flow sensor 120 is capable of providing closed-loop flow control for pump mechanism 114 to achieve and maintain a desired flow rate. Additionally, flow sensor 120 may be able to detect if infusion needle 122 is blocked or that the infusion site is prohibiting a desired drug infusion rate. In an exemplary embodiment, upon detection by flow sensor 120 that the infusion site may be blocked, controller 116 preferably instructs driver 118 to either retract or advance infusion needle 122 to a second infusion depth. Flow sensor 120 may then detect if the desired flow rate is realized at the new infusion depth before potentially alerting the user. This exemplary embodiment may prolong the duration of use of medical device 100 by attempting a new infusion depth that may be capable of providing a desired drug infusion rate, without unnecessarily alerting the user to replace medical device 100.

Figure 4:
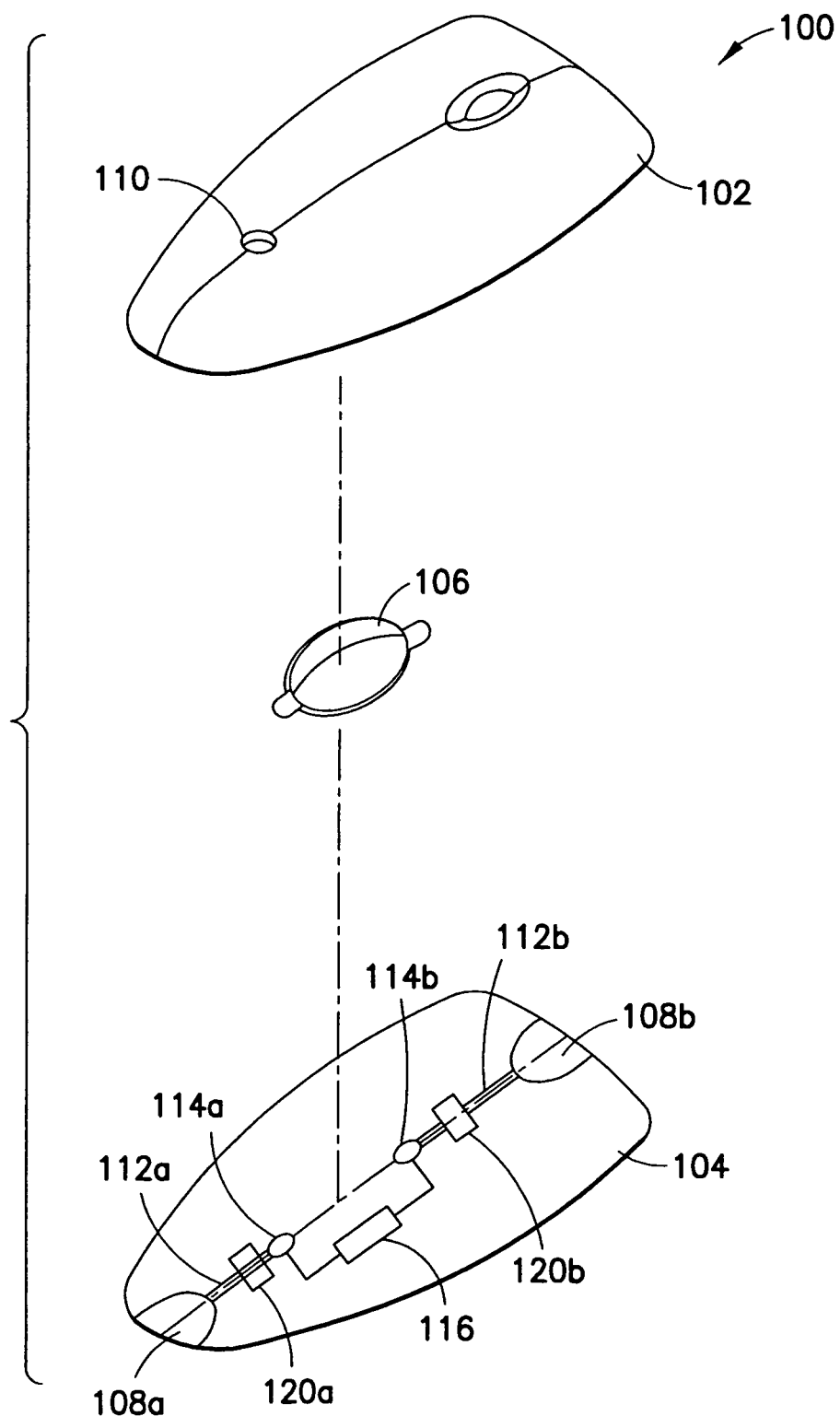
FIG. 4 illustrates a medical device according to another exemplary embodiment of the present invention.
Figure 5:
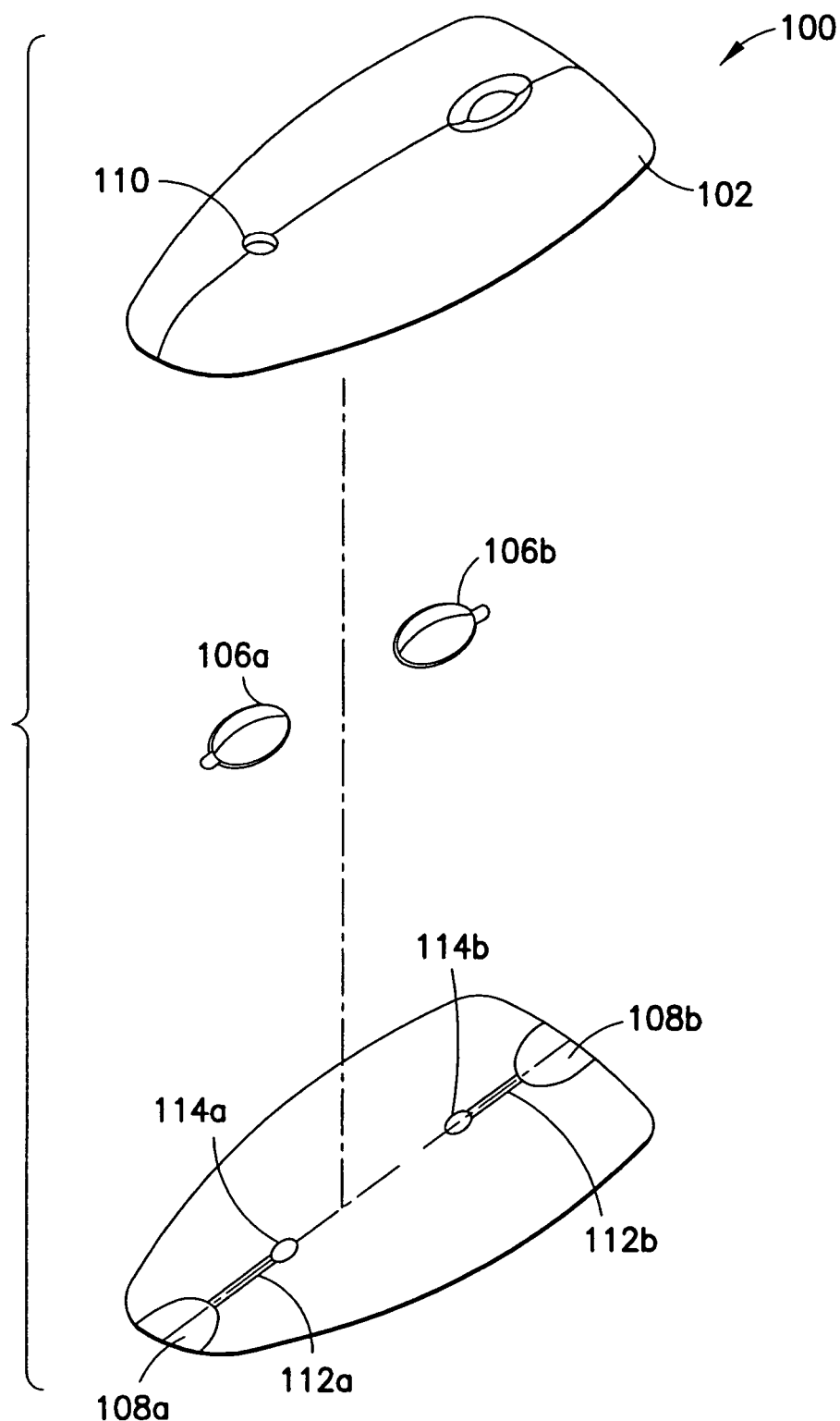
FIG. 5 illustrates a medical device according to another exemplary embodiment of the present invention.

Another exemplary embodiment of medical device 100 for use in the present invention is illustrated in FIGS. 4 and 5. Medical device 100 in FIG. 4 preferably comprises a first infusion needle deployment mechanism 108a and a second infusion needle deployment mechanism 108b. Infusion needle deployment mechanisms 108a and 108b may be actuated independently and are preferably, but not necessarily, located at opposing ends of medical device 100. Infusion needle deployment mechanisms 108a and 108b may be realized in any of the embodiments described above with respect to infusion needle deployment mechanism 108 shown in FIG. 3C. Medical device 100 in this embodiment also preferably comprises at least one flow sensor 120a or 120b for detecting and potentially alerting the user that drug flow through the respective infusion needle is blocked. In an exemplary embodiment, infusion needle deployment mechanism 108a is initially actuated, either manually or automatically, to insert an infusion needle 122 into the user at a desired depth. It is not required in this embodiment, although it may be preferred, that needle mechanisms 108a and 108b are configured to variably advance and retract infusion needle 122 into the user as illustrated in FIGS. 3C-3E. After actuation of needle deployment mechanism 108a to insert infusion needle 122 into the user, flow sensor 120a preferably detects whether drug flow to the user is blocked. If drug flow is determined to be blocked, controller 116 may preferably alert the user and instruct the user to manually actuate infusion needle deployment mechanism 108b. Alternatively, controller 116 may automatically actuate needle deployment mechanism 108b. After actuation of needle deployment mechanism 108b, controller 116 preferably instructs pump mechanism 114a to stop the flow of a drug through infusion needle 122 of needle deployment mechanism 108a and to commence drug flow to the second infusion site provided by needle deployment mechanism 108b.

Figure 6A:
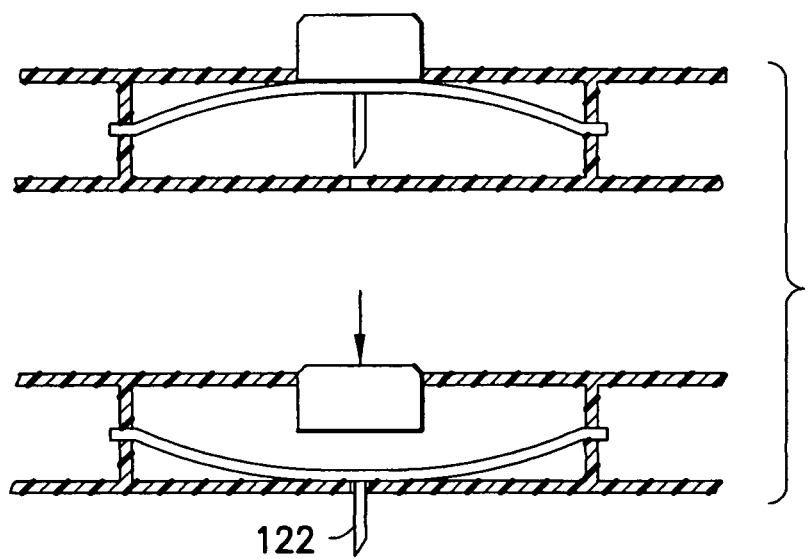
FIGS. 6A-6F illustrate needle deployment mechanisms for use in a medical device according to an exemplary embodiment of the present invention.
Figure 6B:
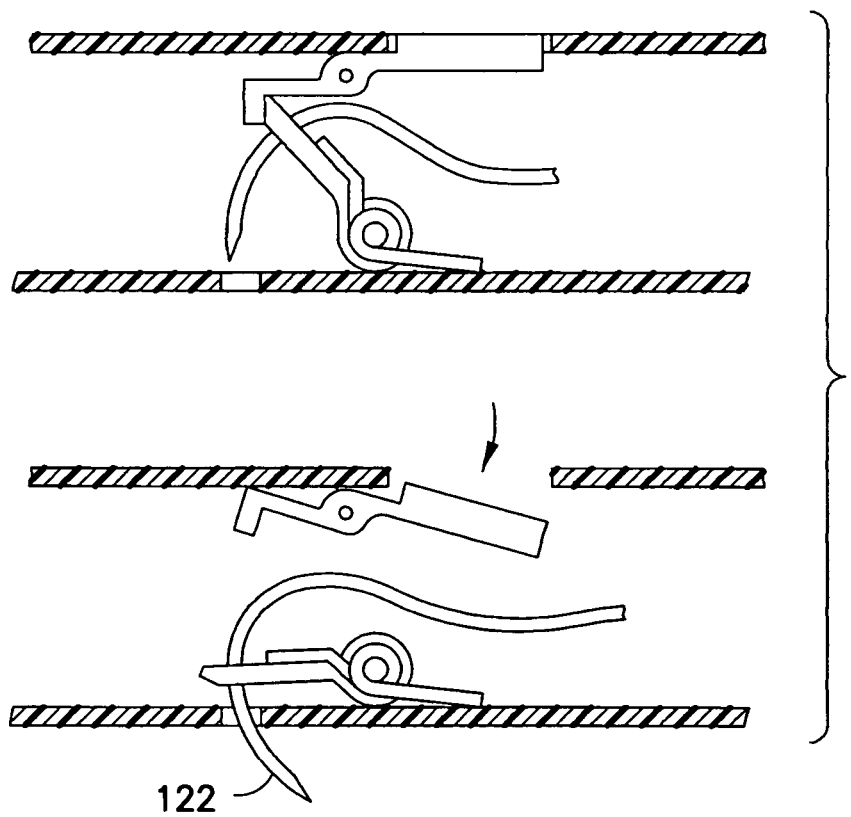
Figure 6C:
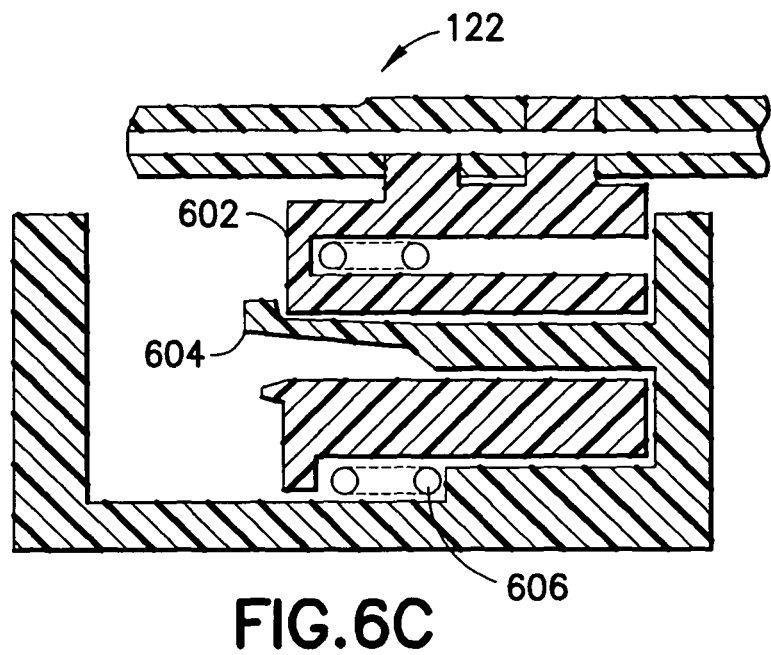
Figure 6D:
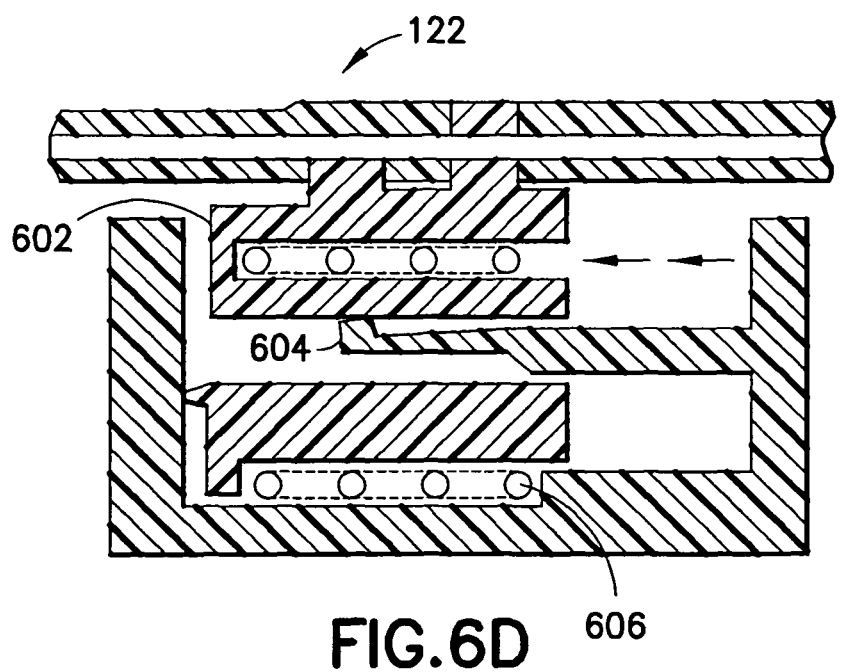

In the above embodiment, since two needle deployment mechanisms 108a and 108b are utilized, it may not be necessary to utilize variable retraction/insertion of the infusion needle 122. Any suitable, either mechanically or automatically actuated needle deployment mechanism may be utilized in this embodiment. Simple, manually actuated one-time deployment needle mechanisms 108a and 108b such as those employing a snap disk or torsion spring shown in FIGS. 6A and 6B may be utilized in this embodiment. FIGS. 6C and 6D illustrate another embodiment for use in the present invention that is especially suitable for the infusion needles 122 shown in FIGS. 3A and 3B. As shown in FIG. 6C, an infusion needle 122 is attached to a needle carriage 602. Needle carriage 602 is held in a retracted, ready position by a retention latch member 604, which prevents needle carriage 602 from movement in the insertion direction. Infusion needle deployment may be actuated manually or automatically to displace the retention latch member 604 from a blocking position. When retention latch 604 is actuated, a compression spring 606 drives needle carriage 602 in an insertion direction, as shown in FIG. 6D. After infusion needle 122 is inserted into the user, distal movement of needle carriage 602 is impeded by a chassis or housing containing the needle deployment mechanism.

Figure 6E:
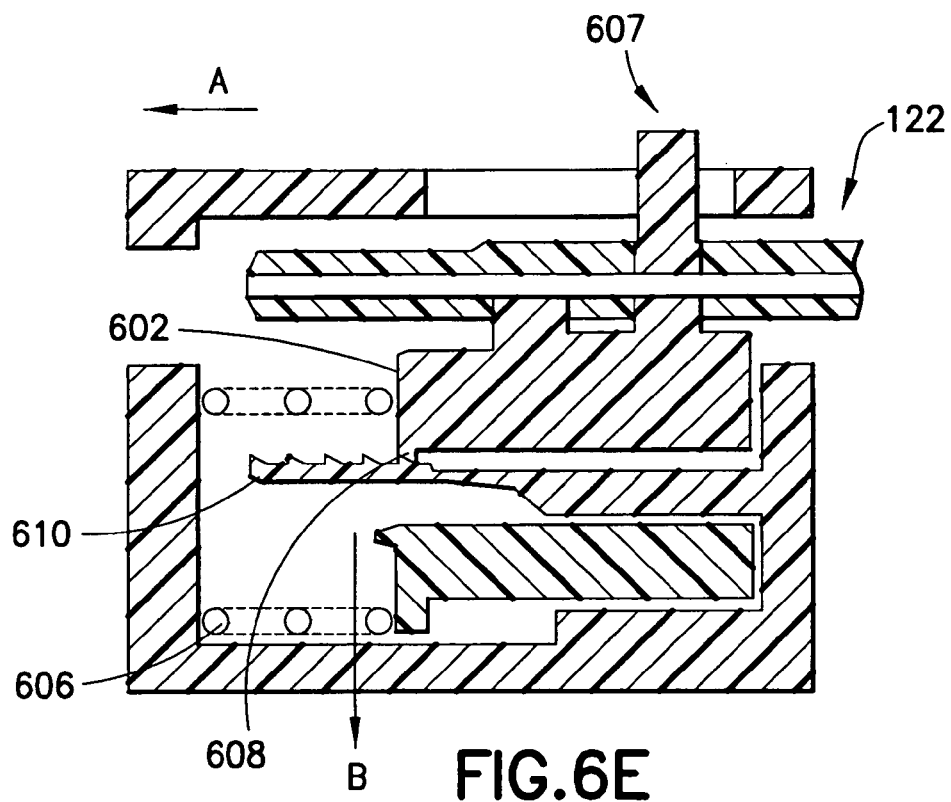
Figure 6F:
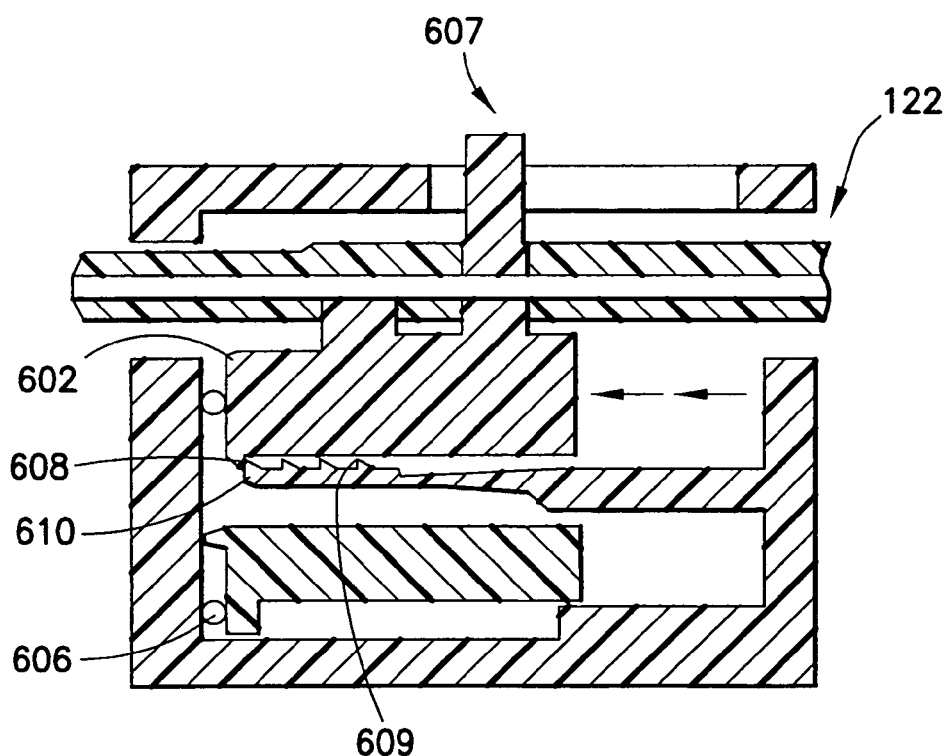

FIGS. 6E and 6F illustrate another deployment mechanism for an infusion needle for use in a medical device according to an embodiment of the present invention. Rather than being triggered as in previously described mechanisms, the needle deployment can be user controlled. That is, carriage 602 is biased in a retracted position by compression spring 606. FIG. 6E shows the device in the retracted position, such that infusion needle 122 does not protrude from the chassis. Carriage 602 includes a manual actuator 607 which is accessible to the user. When the user moves manual actuator in the direction of arrow 'A' with enough force to overcome the spring bias, the carriage 602, along with infusion needle 122 move in the direction of arrow 'A'. Carriage 602 also includes a finger latch 608 which mates with retention surfaces 609 on retention latch 610. As carriage 602 moves in the direction of arrow 'A', interference between finger latch 608 and retention surfaces 609 cause retention latch 610 to displace in the direction of arrow 'B'. Finger latch 608 and retention surfaces 609 are shaped such that as the finger latch moves past each retention surface 609, carriage 602 is prevented from moving backwards in the retracted direction. As the carriage moves in the direction of arrow 'A' the infusion needle protrudes from the chassis and enters the user's skin surface. Cantilevered retention latch 610 can be flexed downward in the direction of arrow 'B' to release the carriage 602 and retract the infusion needle. As will be appreciated by those of ordinary skill in the art, any suitable arrangement to release carriage 602 by flexing retention latch 610 downward may be employed. Such arrangements may include manual movement by the user via a device provided on the exterior of the chassis, or automatic electronic release via an appropriate command on a PDM.

Figure 6G:
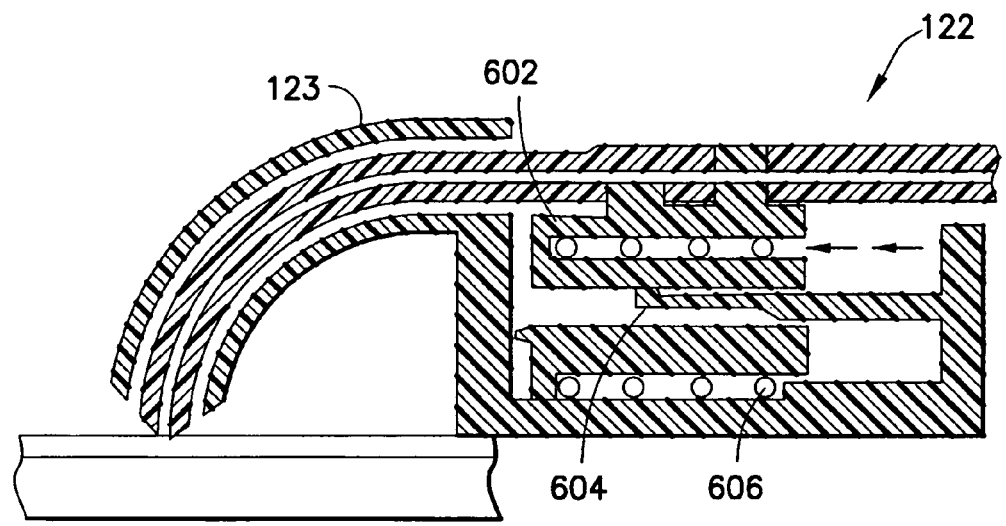
FIGS. 6G-6H illustrate an additional exemplary embodiment of the needle deployment mechanism shown in FIGS. 6C-6F for use in any of the exemplary embodiments of a medical device.
Figure 6H:
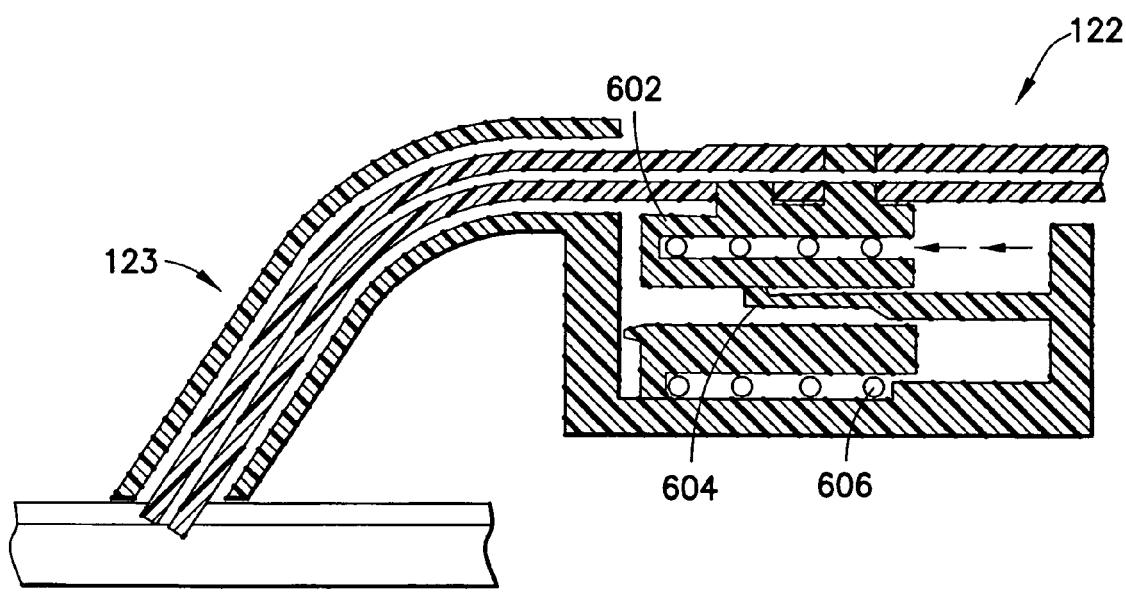

FIGS. 6G and 6H illustrate the needle deployment mechanism of FIG. 6C discussed above with a guide sleeve 123 for guiding the flexible infusion needle 122 into the user at a desired insertion angle. Additionally, guide sleeve 123 provides additional integrity for the flexible needle 122 so as to resist kinking or other undesirable deflection during deployment. As should be appreciated from FIGS. 6G and 6H, guide sleeve 123 can be configured within the medical device to enable deployment in various orientations with respect to the motion of needle carriage 602. As such, the use of guide sleeve 123 in the exemplary embodiments enables deployment of infusion needle 122 into the skin while minimizing the affect of the needle deployment mechanism on the overall profile of the medical device, by permitting the carriages to move parallel to the skin.

As shown in FIGS. 4 and 5, medical device 100 may comprise two separate pump mechanisms, 114a and 114b to control infusion to the user at an infusion site provided by needle deployment mechanisms 108a and 108b, respectively. Alternatively, it should be appreciated by one of ordinary skill in the art that a single pump mechanism 114 may be provided to pump a drug to the user at each activated infusion site. Pump mechanism 114 may preferably be a piezoelectric diaphragm, or a thermal bubble micro-pump described in previously incorporated co-pending U.S. patent application titled "Flexible and Conformal Patch Pump," as well as any other suitable and well known pump mechanism. One of ordinary skill in the art would recognize that controller 116 may drive needle deployment mechanism 108a to insert or retract the infusion needle 122 to a second infusion depth, as discussed in a previous embodiment, before alerting the user or automatically actuating needle mechanism 108b. In this exemplary embodiment, infusion needle mechanism 108b provides a redundant infusion needle to enable therapy to continue at a second infusion site if flow to a first infusion site becomes blocked. It may also be appreciated by one of ordinary skill in the art, that needle deployment mechanism 108b may be actuated in other circumstances as well, such as after a predetermined period of use of the first infusion site or if the first infusion site becomes irritated or inflamed.

An additional feature to be used in any of the above embodiments provides a means for heparinizing infusion needle 122. Heparinization of infusion needle 122 may be performed prior to initial insertion into the user's skin or during the variable insertion and retraction motions. Heparinization may be performed by coating infusion needle 122 with heparin by any method available to one of ordinary skill in the art. A heparinized infusion needle may facilitate preservation of the infusion site by preventing blood coagulation at the infusion site which may block or otherwise complicate the infusion site. The drug Heparin is one in a family of anti-coagulants. One of ordinary skill in the art would appreciate that similar drugs can be substituted to achieve the same benefits without departing from the scope and spirit of this embodiment of the present invention.

By preserving an infusion site provided by a single needle mechanism 108, employing a second needle mechanism 108b, or a combination of each, medical device 100 is capable of extending drug therapy for the user over other available patch pumps in the art. The modifications and enhancements necessary for providing the extended functionality do not significantly increase the complexity of medical device 100 and may be provided with simple, cost effective components. While the unit cost of a single medical device 100 may increase slightly, the extended duration of use provided by the additional components necessarily reduces the daily cost of providing drug therapy to the user through medical device 100, and necessarily reduces waste.

Providing a medical device 100 capable of extending drug therapy to a user, as described in any of the exemplary embodiments discussed above, introduces a unique challenge for supplying an adequate volume of a drug to the user over the extended use of the medical device. FIGS. 1, 4 and 5 illustrate preferred embodiments for providing a reservoir 106 that houses or stores the drug supply.

Exemplary embodiments of medical device 100 employing a single infusion needle mechanism 108 preferably comprise a single reservoir 106 as shown in FIG. 1A. In a first embodiment, reservoir 106 is capable of housing a volume of drug that provides an adequate supply for the extended duration of use, such as 5-7 days. In this embodiment, reservoir 106 may be provided as a prefilled reservoir packaged in medical device 100. Reservoir 106 is preferably integral with the patch pump and requires no additional steps to transfer or engage the drug supply to medical device 100. Reservoir 106 may be provided as a rigid or flexible structure and is preferably constructed from materials such as a TOPAS® (Thermoplastic Olefin Polymer of Amorphous Structure) COC (cyclic olefin copolymer), COP (cyclic olefin polymer) or CCP (crystal clear polymer), which is a material registered by Becton, Dickinson and Company, and listed by the U.S. Food and Drug Administration as DMF No. 16368. Any other well known materials suitable for housing a drug may also be used in the present invention.

Figure 7A:
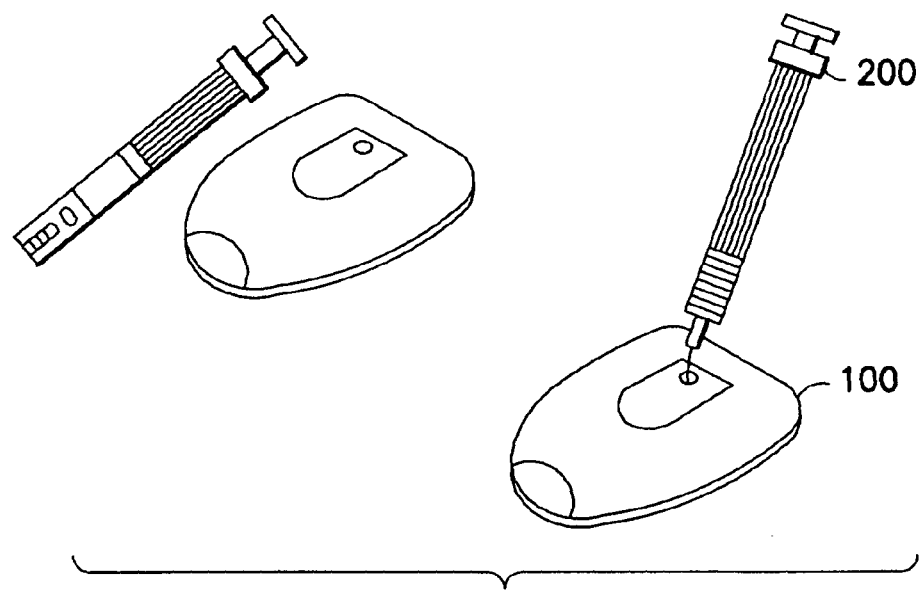
FIG. 7A illustrates a fillable/refillable reservoir in a medical device according to an exemplary embodiment of the present invention.

In another embodiment, as shown in FIG. 7a, reservoir 106 may comprise a fillable and/or refillable reservoir contained in medical device 100. In this embodiment, a user may transfer the drug into reservoir 106 through a fill port 110 or septum preferably provided on an outer surface of medical device 100. Conventional patch pump kits typically include a syringe for transferring a drug from a pharmaceutical vial into the reservoir. Alternatively, an exemplary embodiment of the present invention provides a pre-filled syringe 200 or pre-filled syringe cartridge containing a specific amount of drug suitable for the volume of reservoir 106 or custom to a user's needs. The pre-filled syringe and syringe cartridge may be included as part of a patch pump kit or as part of a package of pre-filled syringes. Such embodiments necessarily reduce the complexity of using medical device 100 and may further reduce the daily cost of therapy in using such device.

Figure 7B:
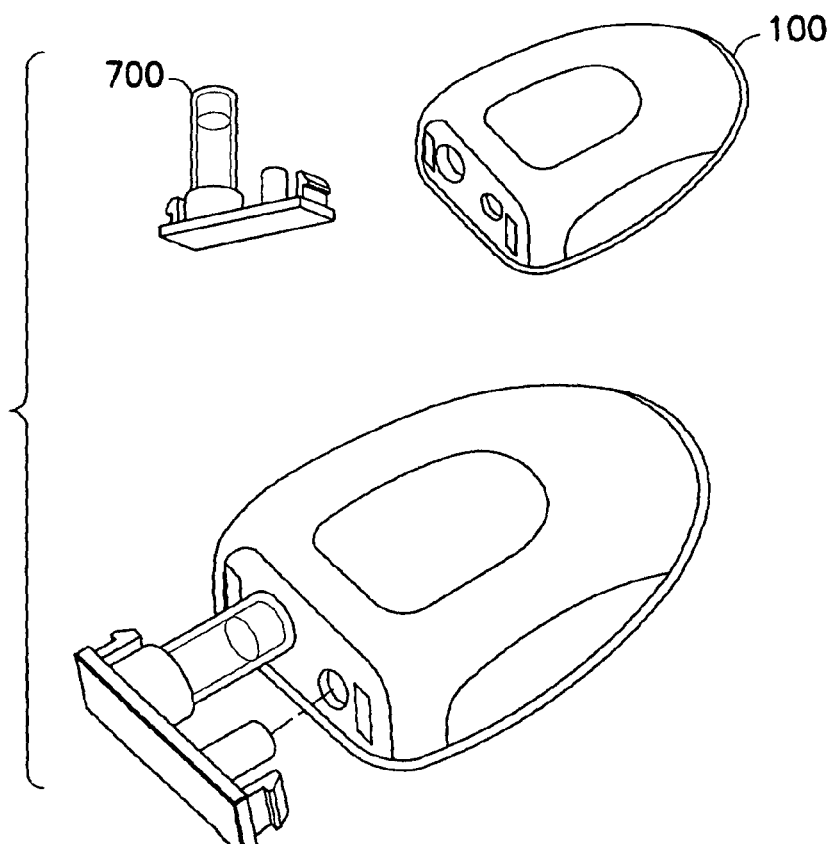
FIG. 7B illustrates an insertable/replaceable reservoir assembly in a medical device according to an exemplary embodiment of the present invention.

Another exemplary embodiment, as shown in FIG. 7b, comprises a pre-filled reservoir assembly 700 or cartridge that is separable from medical device 100. In this embodiment, the user would engage the pre-filled reservoir assembly 700 into medical device 100, and that action would connect the pre-filled reservoir to the pump mechanism of medical device 100. The capacity of a fillable/refillable reservoir 106 or pre-filled reservoir assembly 700 described in the above embodiments may be determined by the construction of medical device 100 and its required use for a particular user. Since the reservoirs in these embodiments are refillable or replaceable, it is not required that their capacity be adequate to supply a drug for the entire duration of use of medical device 100. However, it is preferred that reservoir 106 is of sufficient capacity that it may only need to be refilled or replaced once throughout the duration of use of medical device 100.

FIGS. 4 and 5 illustrate exemplary embodiments of reservoir 106 provided in medical device 100 comprising first and second infusion needle deployment mechanisms 108a and 108b. Reservoir 106 in FIG. 4 can be implemented the same as the embodiments provided above to supply a drug for both needle deployment mechanisms 108a and 108b. However, due to the increased number of components as a result of the second infusion needle deployment mechanism 108b, in order to conserve space, it is preferred that reservoir 106 in FIG. 4 contain a reduced capacity and be refillable/replaceable over the duration of use of medical device 100 as described above. The embodiment illustrated in FIG. 5 comprises two reservoirs, 106a and 106b. In this embodiment, reservoir 106a is provided to supply a drug strictly to needle mechanism 108a and reservoir 106b is provided for supplying a drug to needle mechanism 108b. Reservoir 106a and 106b are preferably prefilled, but may also be fillable/refillable or insertable/replaceable as disclosed above.

The above exemplary embodiments reduce the daily cost of infusion delivery by extending the duration of use of wearable patch pumps that are typically entirely disposed of after their use. Medical device 100, in the above embodiments, includes system components that may safely be re-used. Thus, completely disposing of the medical device causes unnecessary waste of useful, relatively expensive components. The daily cost of infusion delivery for such patch pumps may even be further reduced by providing a medical device in the above exemplary embodiments that re-uses the relatively expensive components. Only those components that may safely be re-used are preferably contained in a reusable portion of the medical device, while any unsafe or single use components are preferably contained in a disposable portion.

Figure 8A:
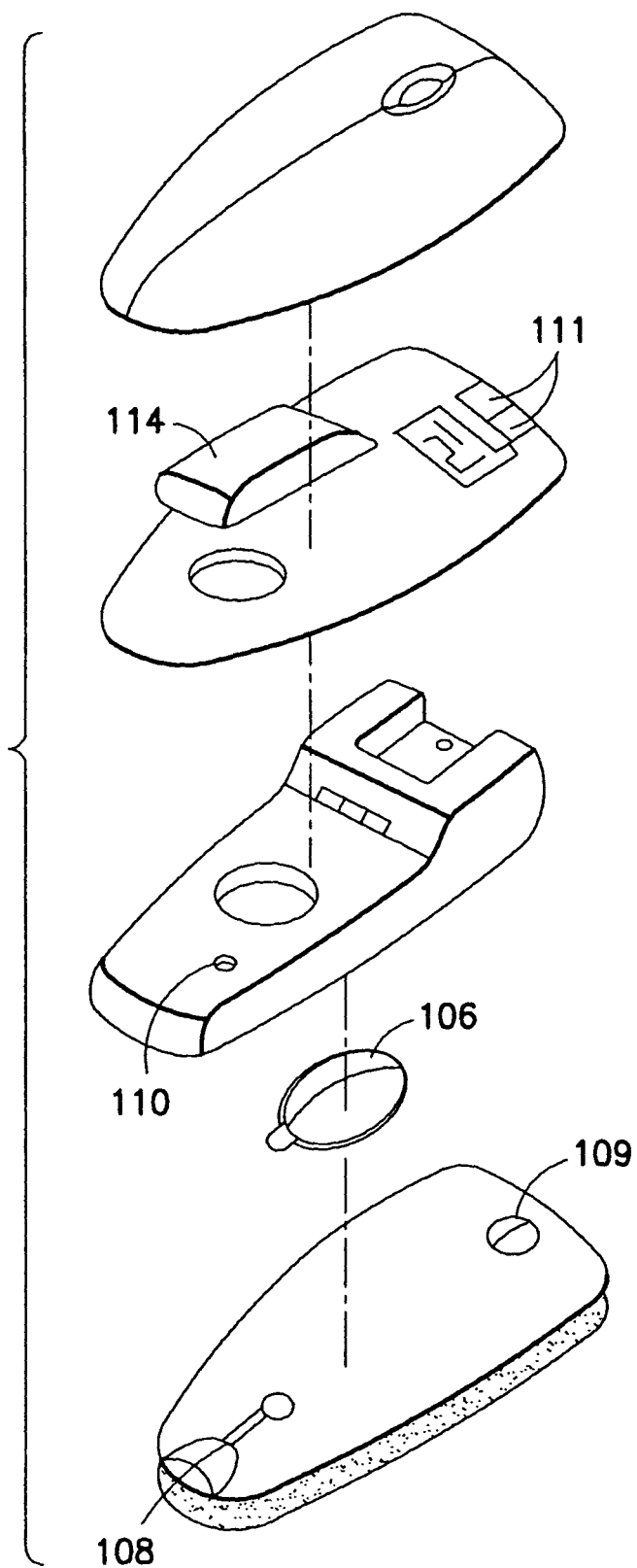
FIGS. 8A-8B illustrate partially reusable/partially disposable medical devices according to exemplary embodiments of the present invention.

An exemplary embodiment of the present invention, as illustrated in FIG. 8A, provides a partially reusable and partially disposable medical device 100 in accordance with any of the above exemplary embodiments. In an exemplary embodiment, medical device 100 is designed such that only the "sterile" or "spent" components are replaced after each duration of use as described in previously incorporated U.S. Pat. No. 6,589,229 issued to Robert I Connelly, et al. For instance, the components which should be replaced after each use include: the infusion needle 122, the drug reservoir 106, an adhesive for affixing medical device 100 to the user and an optional battery or power source 109. In some embodiments, the disposable housing may further comprise a flow sensor 120 for detecting a rate of drug flow to the user or any blockage of flow at the infusion site in accordance with the exemplary embodiments described above. These components are preferably encapsulated in a two-piece sealed housing with exposed interfaces for needle deployment mechanism 108, pump mechanism 114 and electrical contacts 111 for electronically connecting the flow sensor 120 and optional battery 109 to controller 116. Drug reservoir 106 may be implemented as described in any of the exemplary embodiments above. If reservoir 106 is fillable/re-fillable, a fill port 110 or septum is preferably provided on the disposable housing.

In an exemplary embodiment, controller 116, pump mechanism 114, and needle deployment mechanism 108 are preferably housed in a separate reusable structure 130 of similar design as a disposable portion 132. The disposable portion 132 preferably latches together with the reusable portion 130, thus automatically engaging controller 116, pump mechanism 114 and needle deployment mechanism 108 with the optional battery 109 and flow sensor 120, drug reservoir 106 and infusion needle 122, respectively. It should be appreciated by one of ordinary skill in the art, that any of the above exemplary embodiments of medical device 100 may be provided a reusable housing portion and a disposable housing portion. To ensure that the disposable portion 132 of medical device 100 is not used beyond the predetermined duration, in an exemplary embodiment of the present invention, controller 116 may be enabled to alert the user that the disposable portion should be replaced. After a specific number of alerts, controller 116 may further be enabled to disable the disposable portion 132. The reusable components may include a needle deployment mechanism, device electronics or system intelligence, a fluid metering device or pump, and any housing components necessary for guidance, alignment, engagement, or latching and unlatching with the disposable portion. If desired, a rechargeable power source or other energy harvesting components may also be included within the reusable portion 130. The reusable portion may also be configured with the necessary components to communicate with any other smart device using a personal area network, or other communication technology as disclosed in previously incorporated U.S. patent application Ser. No. 12/458,807. Information that may be communicated includes any system diagnostic information, and a stored history of a user's infusion rate and schedule information. The specific components contained in the reusable and disposable housing are dependent on the preferred application of medical device 100 and are not limited to the embodiments described above. One of ordinary skill in the art would appreciate that any combination of components and features may be provided in each, as desired by the user.

In a preferred embodiment, the reusable portion 130 is configured and constructed for repeated use with a disposable portion 132 for a duration of two years or more. During this time frame, the electrical interconnections 111 between the reusable and disposable portion are susceptible to failure. Typical electrical connections are brittle and may not withstand the type of use or period of use the medical device is intended for. One exemplary embodiment of the present invention does without the electrical connections 111 and enables a reusable portion 130 to communicate with a disposable portion 132 using the personal area network (PAN) discussed above. The cost for providing a PAN transceiver in the disposable portion 132 is negligible, especially compared with the tradeoff for providing greater durability and extended use of the medical device assembly.

The reusable portion 130 of medical device 100 represents 60%-70% of the entire device cost. Distributing the cost over a predetermined period, such as 360 days or more, would basically reduce the daily cost of drug infusion therapy to the cost of the disposable portion of the device. By further extending the duration of use of the disposable portion 132 of the device in accordance with the above exemplary embodiments, the daily cost is reduced even further.

Figure 9:
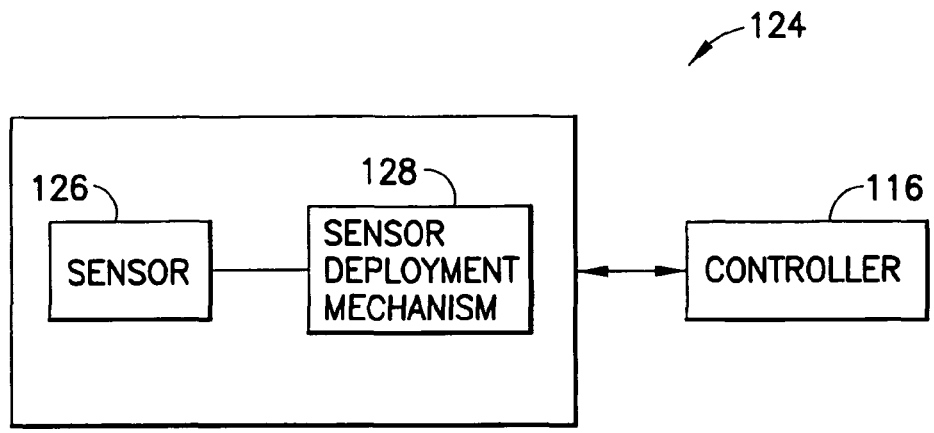
FIG. 9 is a block diagram depicting the principal components of a sensing unit according to an exemplary embodiment of the present invention.

FIGS. 2 and 9 further illustrate another exemplary embodiment of medical device 100 incorporating an optional sensing unit 124 that is enabled by the extended duration of use provided in accordance with the above exemplary embodiments. Specific to diabetes care, the medical industry is migrating toward closed loop systems for insulin infusion. An ideal system, typically referred to as an "artificial pancreas", includes continuous glucose monitoring to provide "real time" or "near real time" feedback for precise insulin infusion control. Continuous glucose monitoring may be realized in sensing unit 124 comprising a sensor 126 for providing data on a user's blood glucose levels.

FIG. 2 depicts sensing unit 124 as being contained in medical device 100. While this is a preferred embodiment, one of ordinary skill in the art would appreciate that sensing unit 124 may be provided separate from medical device 100. Sensor 126 may be embodied as any well known sensing or sampling technology. For instance, some well known sensing technologies employ electrochemical, colorimetric, optical/spectroscopy or other energy based detection methods for determining a user's blood glucose level. In addition, there are two categories of well known sampling technologies, invasive and non-invasive, that may be implemented as well. An exemplary embodiment of the present invention preferably employs a colorimetric sensor sensing glucose binding protein (GBP) or an electrochemical sensor such as a glucose-oxidase (GOx) sensor described in U.S. Pat. No. 7,310,544 to Brister et al., and the analyte sensor disclosed in U.S. Patent Publication No. 2005/0245799 to Brauker et al., each assigned to DexCom Inc. and expressly incorporated herein by reference. The implantable GOx sensor described therein has been shown to provide a duration of use of up to seven days. Accordingly, until now, there has been a paradox in effectively implementing such sensing technology in common wearable patch pumps due to the shorter duration of use of the patch pump, as compared to the sensor. The exemplary embodiments discussed above provide extended use medical devices 100 capable of matching the performance of leading continuous glucose monitoring technologies.

Sensing unit 124, as shown in FIG. 9, preferably comprises a sensor 126 discussed above, and a sensor deployment mechanism 128. Deployment mechanism 128 may be manually or automatically actuated and may be embodied in any of the above described systems for infusion needle deployment mechanism 108. Of course it should be understood that automatic deployment may be effected via an appropriate command received from a BGM, PDM or a host device. The needle deployment mechanisms 108 discussed above, as well as the embodiments described in previously incorporated U.S. patent application titled "Flexible and Conformal Patch Pump," may be easily modified to provide for the insertion of sensor 126. For instance, sensor 126 may be provided at the end of a driving needle or push rod, similar in construction to an infusion needle for inserting sensor 126 into the user's skin. Additionally, sensor 126 may be positioned in the user with the aid of an insertion sleeve that is retracted once the sensor is placed at a desired depth in the user. Sensor deployment mechanism 128 preferably provides a single insertion motion and a withdrawal motion for inserting and withdrawing sensor 126. Sensor deployment mechanism 128, alternately, may also be provided to variably insert and retract sensor 126, as similarly described in an exemplary embodiment above with respect to infusion needle deployment mechanism 108. Inflammation or other bodily response to a foreign object at the sensor insertion site may inhibit sensor 126 from providing critically accurate sensing information. Thus, by adjusting the insertion depth of sensor 126, sensing unit 124 may provide more accurate sensing information, resulting in greater precision of infusion rate and improved comfort for the user. In one exemplary embodiment, sensor deployment mechanism 128 is located at an opposite end of infusion needle mechanism 108. In another embodiment, sensor 126 is co-located with infusion needle 122. Thus, in this embodiment, sensor deployment mechanism and infusion needle deployment mechanism 108 may be embodied in the same structure.

Figure 10A:
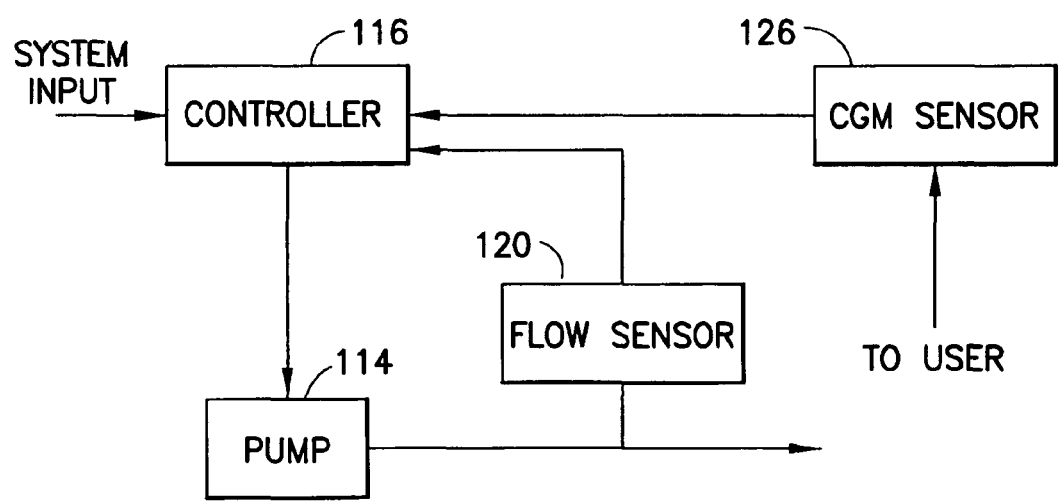
FIGS. 10A-10B are diagrams illustrating the principal operation of a continuous glucose monitoring system according to exemplary embodiments of the present invention.
Figure 10B:
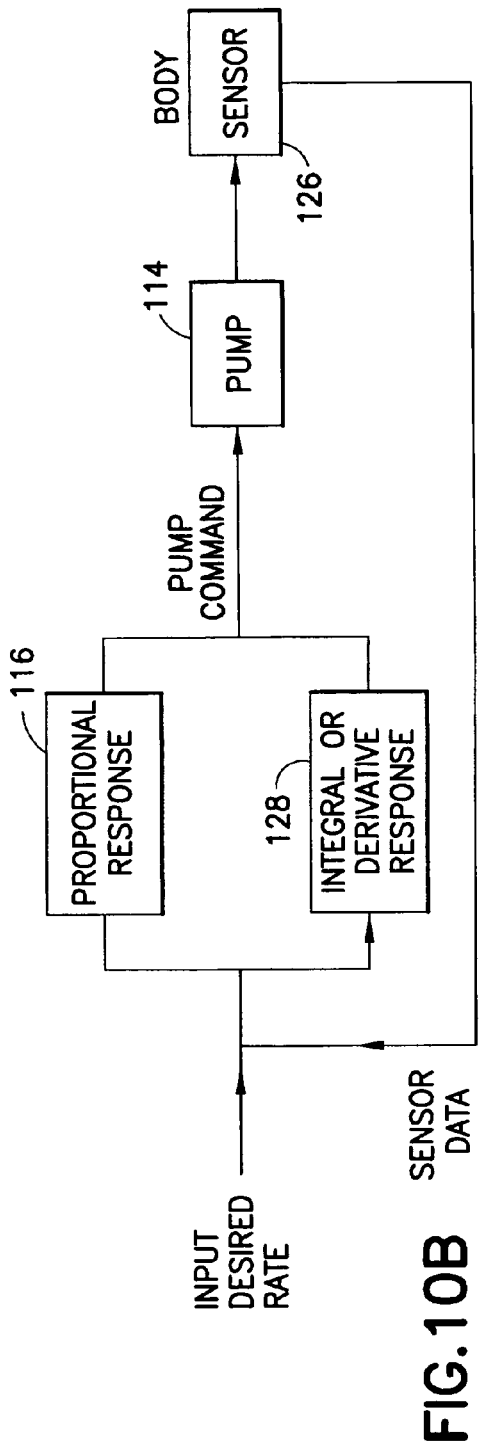

FIGS. 10A and 10B illustrate a system for providing continuous glucose monitoring and infusion rate control in an exemplary embodiment of the present invention. Controller 116 receives as input, data from flow sensor 120 and sensor 126 and accordingly controls pump mechanism 114 to provide a desired infusion rate. A closed-loop infusion control system in accordance with one embodiment of the present invention is described in U.S. Pat. No. 6,558,351 to Steil et al., assigned to Medtronic MiniMed, Inc., which is expressly incorporated herein by reference. The method described therein is directed to a closed-loop infusion control system in which a glucose sensor provides an input signal to a controller, which in turn utilizes a proportional/derivative (PD) component to replicate a first phase insulin response and an integral (I) component to provide a second phase insulin response. PID controllers are well known in the art for providing generic control loop feedback mechanisms using three separate parameters, proportional, integral and derivative. The proportional parameter dictates a reaction to an immediate error in the system. The integral parameter determines a reaction according to a sum of recent errors in the system and the derivative parameter controls a response based on the change in the error rate of the system. The PID controller then determines an appropriate response based on a weighted sum of these parameters. While the PID controller described above may be effective in controlling an insulin infusion rate, each of the PID parameters is not necessary in exemplary embodiments of the present invention.

FIG. 10B illustrates a proportional-integral (PI) or a proportional-derivative (PD) controller for use in exemplary embodiments of the present invention. PI and PD controllers are effective in controlling insulin infusion, since the rate of change for basal infusion is typically extremely small. PI and PD controllers would also provide adequate control for a medical device used to treat Type II diabetes, since the infusion rate in the treatment of Type II diabetes does not need to instantaneously change to a significantly different level. Exemplary embodiments of medical device 100 could provide a motorized pump mechanism 114, such as a linear actuator or a micro motor with integral gear reduction, which may effectively be controlled using a PI or PD controller since the infusion rate does not need to instantaneously change to a significantly different level. Additionally, a stepper controlled motor in which an internal rotor and stator are designed to allow incremental rotation of a shaft or lead screw, and a ring counter which senses revolutions or partial revolutions of a shaft, are both viable control options for pump mechanism 114, since the maximum error or overshoot could be one step or ring increment. Such high resolution linear actuators and motors with integral gear reducers are well known and available in the art, such as those provided by Haydon Switch and Instrument and MicroMo Electronics. However, such systems sized to the application of a low-profile, discreet wearable medical device, as in exemplary embodiments of the present invention, are typically very expensive. Therefore, the cost for such control is currently prohibitive for use in common, disposable, wearable medical devices. A large number of users prefer or require the control and precision afforded in such an embodiment. Thus, there is a need to provide continuous glucose monitoring with the above pump mechanisms 114 in a package that is practical and affordable for the user.

As discussed above in relation to FIG. 8A, an exemplary embodiment of the present invention may incorporate pump mechanism 114, described directly above, in a reusable portion 130 of medical device 100 that is capable of lasting several years. The high-precision pump mechanism 114 described above, is capable of performing repeated use suitable in a reusable embodiment. Thus, the cost for providing a specialized pump mechanism 114, as well as other relatively costly system components, may be distributed over the lifetime of medical device 100.

The exemplary embodiment of medical device 100 preferably also includes the sensing unit 124 for continuous glucose monitoring discussed above. In this embodiment, the reusable housing further comprises the sensor deployment mechanism 128 and the disposable housing contains sensor 126. The electrical contacts 111 on the disposable portion, in an exemplary embodiment would preferably connect sensor 126 to controller unit 116 for providing continuous glucose monitoring. Alternatively, as similarly discussed above, communication can be provided between the sensor 126 and the controller unit 116 using the PAN communication technique, thus the electrical contacts may not be necessary. Since sensor 126, as described above, is capable of lasting up to 7 days imbedded in the user, there is no unnecessary waste of components or cost in providing the sensor in a reusable portion of an extended use medical device 100 in exemplary embodiments of the present invention.

Figure 8B:
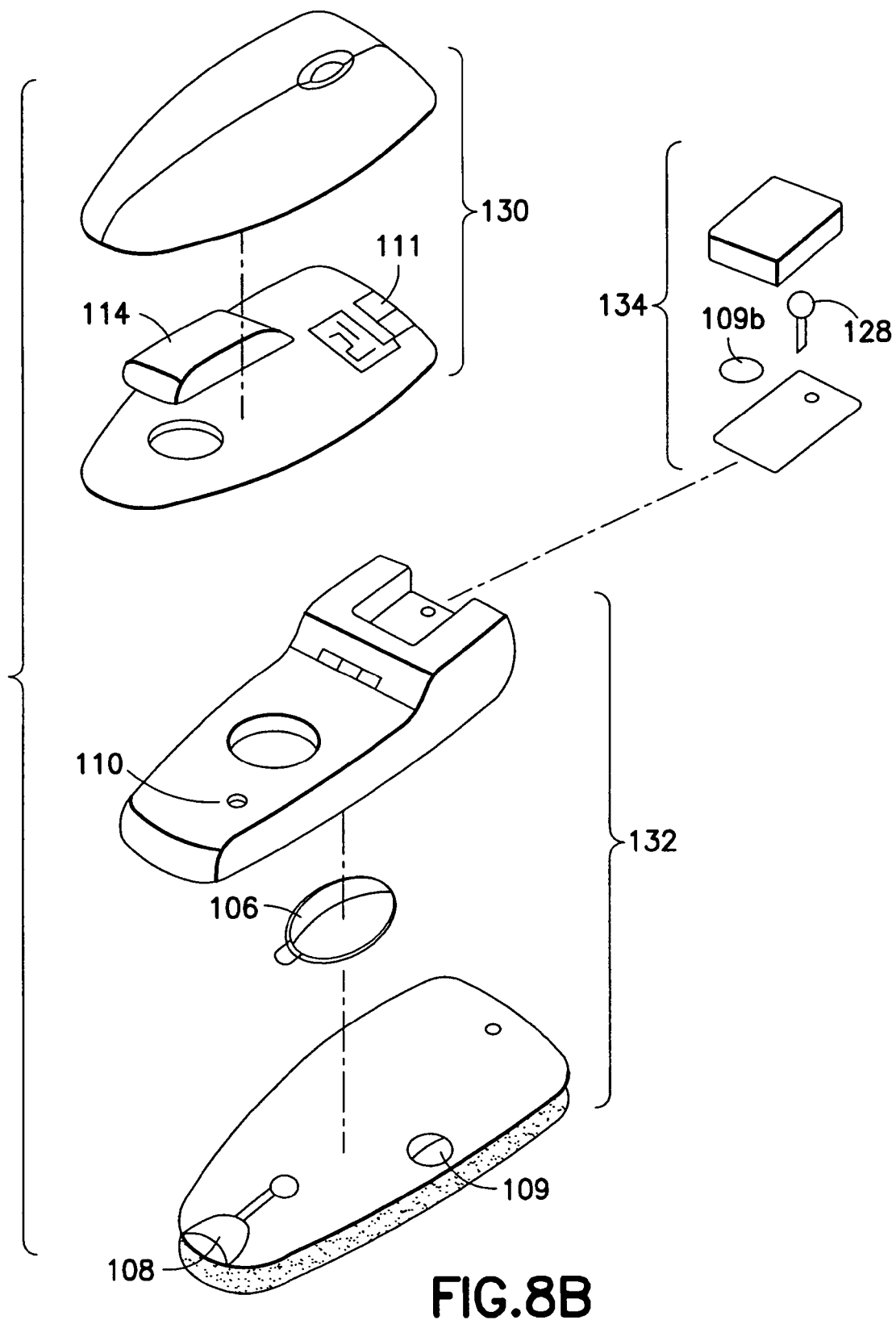

As sensor technology continues to develop, sensor 126 may be capable of providing an even longer duration of use. As such, an exemplary embodiment of the present invention, as shown in FIG. 8B, provides a second, additional disposable portion 134, separate from the disposable portion 132 housing the disposable insulin infusion components, as discussed in relation to FIG. 8A. In this embodiment, the second disposable portion may contain the sensor 126, a sensor deployment mechanism 128 for inserting the sensor and an optional battery 109b as shown. It is preferred that the second disposable portion is provided at an opposite end of the infusion needle mechanism of first disposable portion 132, so as to ensure that the sensor is deployed into viable tissue. Second disposable portion 134 is provided for enabling a longer duration of use for sensor 126, such that the first disposable portion 132 containing components with a lesser duration of use may be disposed of without unnecessarily reducing the span of use of the longer lasting sensor 126. It is preferred that reusable portion 130 and the second disposable portion 134 remain in contact with the user as a first disposable portion 132 is attached to the reusable portion. As discussed above, the second disposable portion 134 can communicate with reusable portion 130 via a direct connection or may be provided with PAN communication components for communicating with reusable portion 130 or other external devices.

Figure 8C:
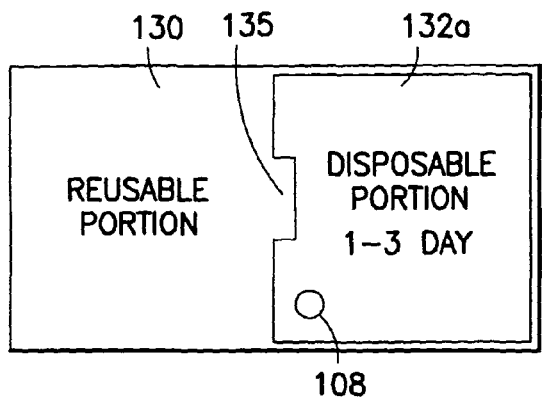
FIGS. 8C-8F illustrate placement of a needle deployment mechanism for use in a partially reusable/partially disposable medical device according to exemplary embodiments of the present invention.
Figure 8D:
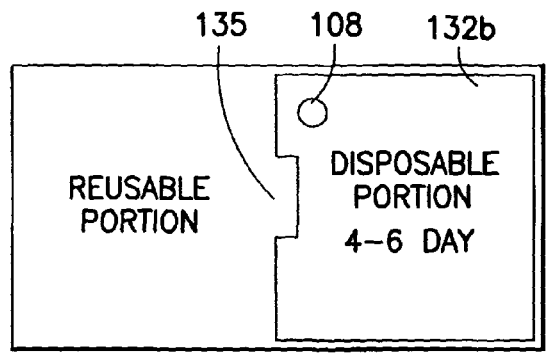
Figure 8E:
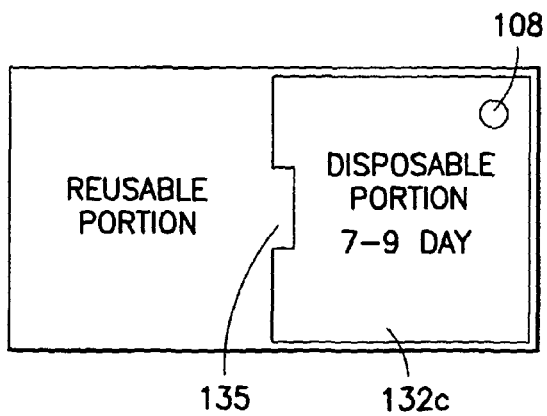
Figure 8F:
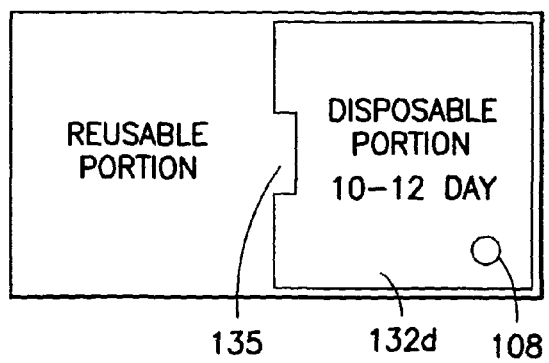

In FIG. 8B, first disposable portion 132 is shown with only a single needle deployment mechanism, however, it may be preferred to provide a second needle deployment mechanism at an opposite corner or end of the disposable portion, as described with respect to FIGS. 4 and 5 for increasing the duration of use of the first disposable portion 132. It is preferred that the second needle deployment mechanism be provided at the opposite corner or end from a first deployment mechanism to provide a fresh viable infusion site at a distance from the first infusion site so as to reduce potential irritation or inflammation at the first infusion site. Additionally, in another embodiment shown in FIGS. 8C-8F, each disposable portion 132a-d obtains a viable infusion site by positioning the respective needle deployment mechanism at a distance from previous needle deployment mechanisms. As reusable portion 130 and second disposable portion 134 remain attached to the user, first disposable portions 132a-d are repeatedly attached to the reusable portion 130 at a disposable housing engagement site. In the first instance of attaching disposable portion 132a, shown in FIG. 8C, needle deployment mechanism 108 is provided in one of the corners of the disposable portion 132a. In FIG. 8C, needle deployment mechanism 108 is provided at the lower left corner. When the short term components of disposable portion 132a are spent, a new, replacement, first disposable portion 132b is attached to reusable portion 130. In disposable portion 132b, the needle deployment mechanism is provided at a different corner of the disposable portion 132b. As shown in FIG. 8D, needle deployment mechanism 108 is provided in the upper left corner of disposable portion 132b. The placement of each needle deployment mechanism in the disposable portions 132a-132d realizes an infusion site between 0.5 and 2.5 inches apart and preferably about 1.25 to 1.75 inches from each other infusion site. The order of use of each disposable portion 132a-132d may be determined by the user so long as the needle deployment mechanism of the disposable portion realizes a new infusion site. Disposable portions 132a-132d preferably include a "key" feature 135 which requires a specific orientation of attachment of one of the disposable portions with the reusable portion 130. As such, this key feature will inhibit the user from attaching a disposable portion to the reusable portion at an orientation that will reuse an infusion site.

Figure 11A:
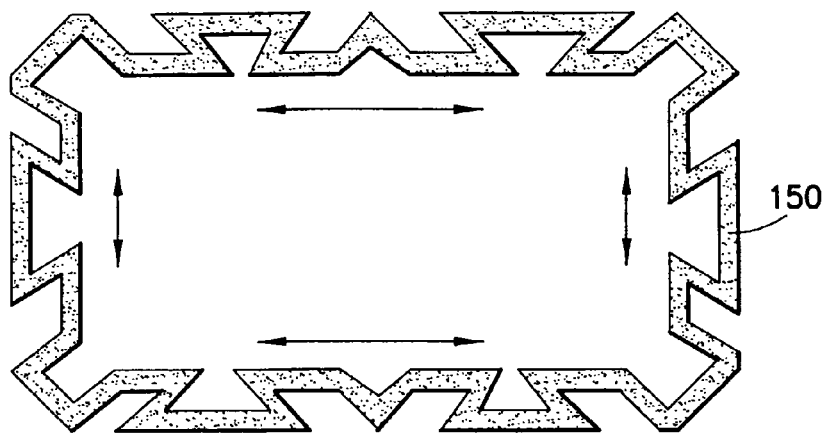
FIGS. 11A-11C illustrate exemplary embodiments of an adhesive design for affixing a medical device to the user according to an exemplary embodiment of the present invention.
Figure 11B:
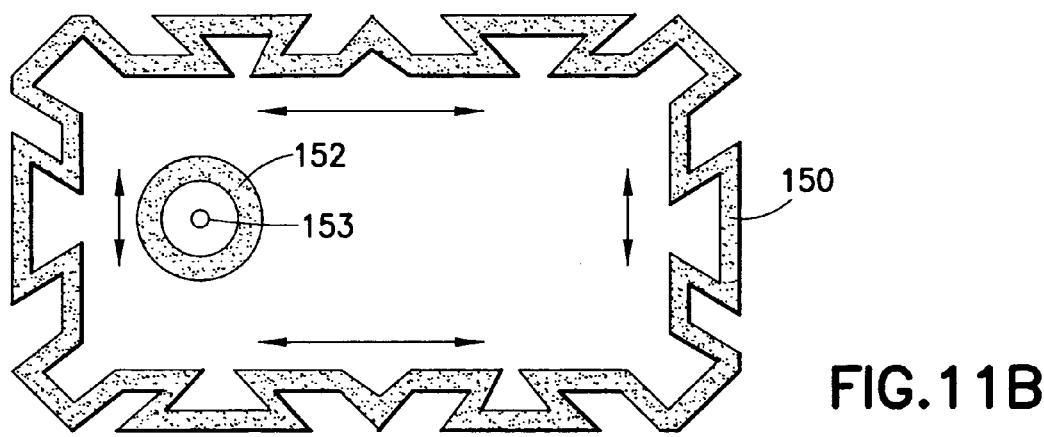
Figure 11C:
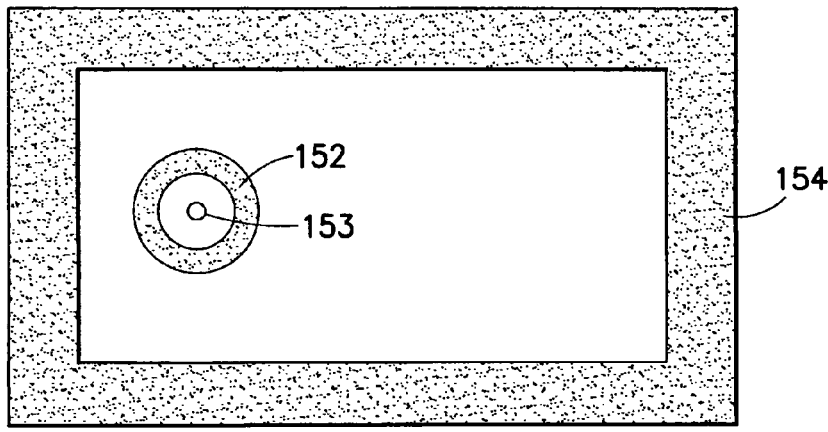

The features of the exemplary medical devices discussed above are provided for extending the duration of use of a wearable medical device. Common wearable medical devices are affixed to a user's skin with an adhesive layer that substantially covers the entire surface area of the portion of housing that is affixed to the user, or is typically provided as an outline of the perimeter of the medical device. However, the common configuration of an adhesive layer may not be suitable for an extended use medical device provided in the above exemplary embodiments. Namely, common adhesive techniques provide very little freedom of movement at the interface between the medical device and the pliable, stretchable skin surface of a user. Over an extended use, the common adhesive layer may not withstand the subtle stretching of the user's skin at this interface or may prove to be too uncomfortable for the user. As such, the adhesive layer 150 shown in FIG. 11A, provides a pattern for enabling increased freedom of movement at the interface of the user's skin and an exemplary medical device, such as a zig-zag pattern. Such a pattern reduces a user's awareness of the physical sensation accompanied by the adhesive interface and extends normal use by allowing subtle movement to occur on the surface of the skin during normal physical activity. It is preferable that the adhesive layer comprise a continuous pattern so as to also provide a seal to protect against water ingress. The adhesive layer is also preferably formed or formulated from a flexible material enabling subtle stretching as indicated in FIGS. 11A and 11B. It is preferred, that the freedom of movement provided by adhesive 150 is subtle and should not cause undesirable movement at the infusion site. Nevertheless, in one embodiment, an additional less-flexible adhesive ring or perimeter 152, acting as an anchor, may be provided at the infusion site 153 for preventing any undesirable movement at this site, as shown in FIGS. 11B and 11C. In such an embodiment, it is preferred that adhesive ring 152 has a higher adhesive property and reduced flexibility relative to adhesive layer 150 or 154. As such, flexibility and comfort of the adhesive layer along the perimeter of the medical device can be maintained without compromising the infusion site 153. Additional embodiments may also comprise an adhesive layer 150 or 154 not only with lower adhesive properties, but also with an increased thickness, or an elastomer or foam layer sandwiched between the adhesive layer and the medical device for providing additional freedom of movement. The pattern shown in FIGS. 11A and 11B is not limiting. Any such zigzagged or curvy type pattern of an adhesive may be provided to enhance the extended wearability of medical device 100 according to the exemplary embodiment. Further, as shown in FIG. 11C, an adhesive layer 154 outlining the perimeter of the medical device may also achieve the desired flexibility discussed above by utilizing reduced adhesive properties, increased flexibility and/or thickness of the adhesive layer as well as implementing the elastomer or foam layer sandwiched between the adhesive layer and the medical device. In this embodiment, it is not necessary that the adhesive layer 154 adopt a zigzagged, curvy or otherwise non-uniform continuous pattern.

Figure 12B:
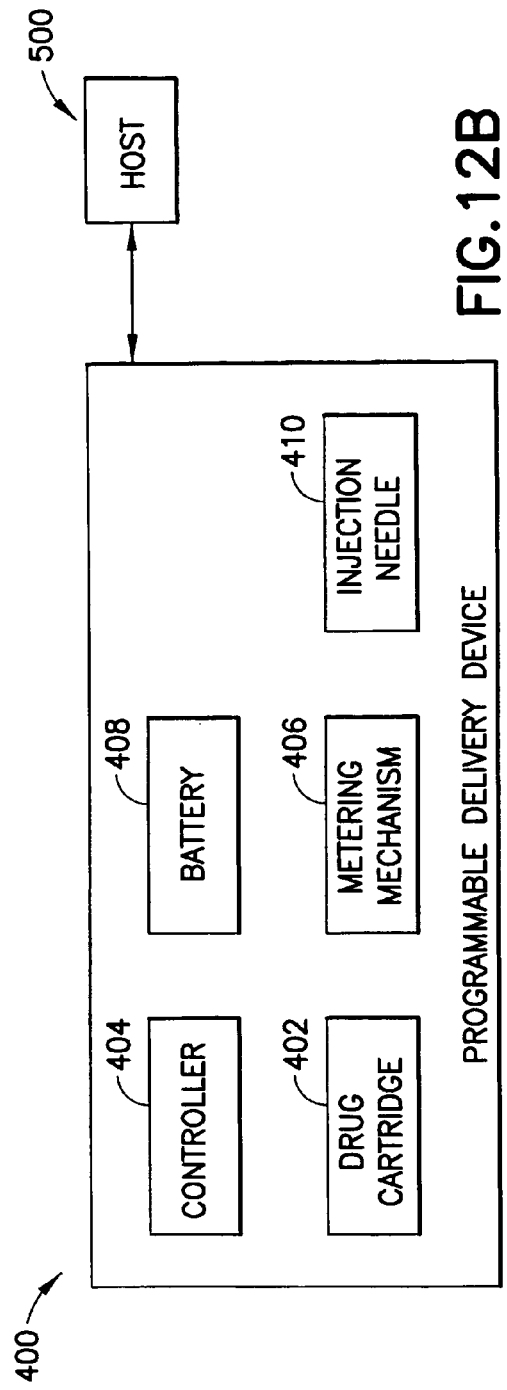
FIGS. 12A-12B illustrate an additional embodiment of a programmable drug delivery device used in conjunction with a medical device according to exemplary embodiments of the present invention.
Figure 12A:
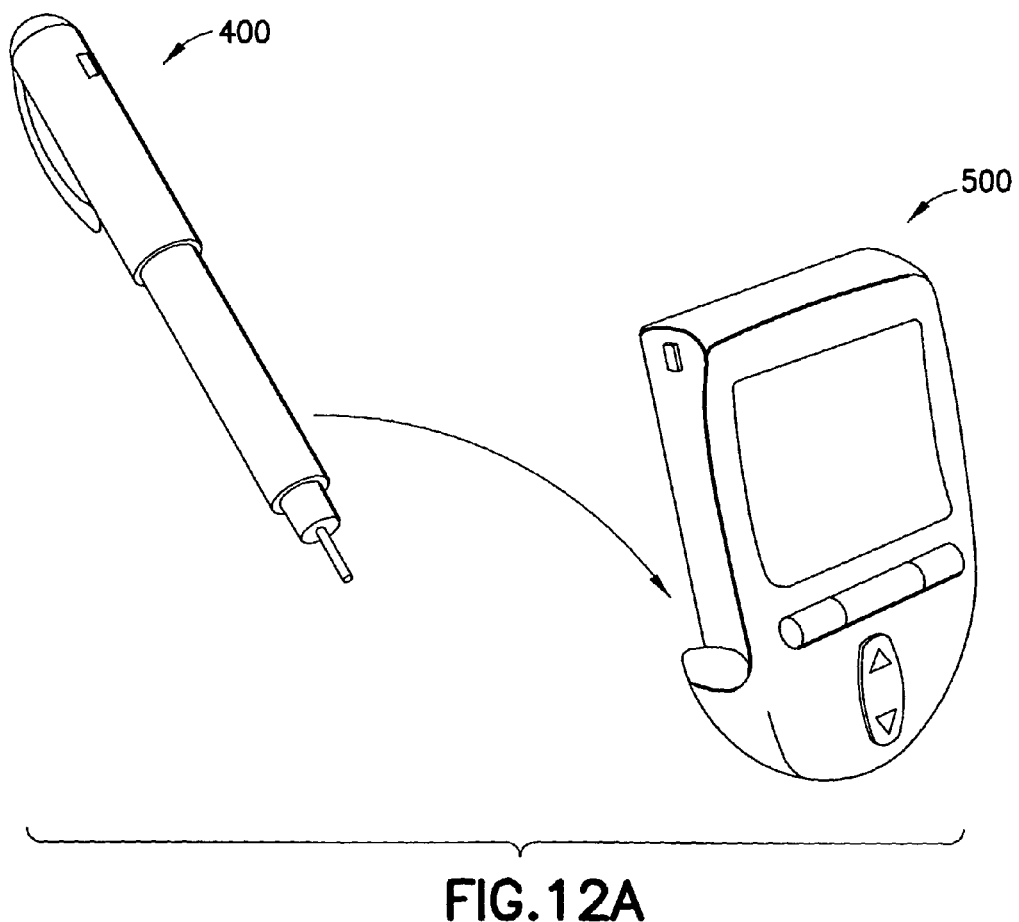

Medical device 100, in any of the exemplary embodiments described above, may also be used in conjunction with a programmable drug delivery device 400, such as a programmable insulin pen, as shown in FIGS. 12A-12B. In a preferred embodiment, a wearable medical device is configured to provide only a preset, pre-programmable or programmable basal rate of infusion, whereas programmable drug delivery device 400 is provided for infusing necessary bolus dosages. While certain embodiments of the wearable medical devices discussed above are capable of providing a bolus dose, some users may be more comfortable with and prefer to use a familiar pen injection device such as that shown in FIG. 12A. Additionally, for some users, drug therapy provided by an insulin pen device alone, may be an effective treatment. Common mechanical insulin pen injection devices typically require user interaction to accurately set a desired dosage for the injection. Conventional mechanical pens generally include small dosage graduations that may be difficult to see or accurately set. As such, a programmable insulin pen device 400, in exemplary embodiments of the present invention would eliminate the potential for dosage errors resulting from a user's inability to properly operate the device.

In one embodiment of the present invention, when not in use, drug delivery device 400 preferably remains attached to a Personal Diabetes Manager (PDM) 500, Blood Glucose Monitor (BGM), or other device for calculating a bolus dose. When a user instructs PDM 500 to calculate a bolus dose requirement, the PDM calculates the dose from either a basal rate infusion history, a user's blood glucose level determined from a standard test strip or communicated by a bodily function sensor, or information about a meal the user will consume, and automatically programs the dose into drug delivery device 400 without any further calculation, setting or adjustment required by the user. PDM 500 may preferably comprise a sensing mechanism or other system for determining a blood glucose level, which it uses to calculate a desired bolus dose for the user. This exemplary embodiment of the present invention reduces the number of steps necessary for infusion and reduces dosage errors caused by a user's inability to properly operate common, mechanical insulin pens.

Drug delivery device 400 in an exemplary embodiment, preferably includes a replaceable insulin cartridge 402 and may be cylindrical in form, similar to insulin pens that are commonly available. The dose mechanization typically located in the upper portion of common insulin pens is preferably replaced by a flex circuit which is wrapped around the inner diameter of the pen barrel. The flex circuit functions as a controller 404 for controlling a drug metering mechanism, such as a micro-pump 406 or motor, to deliver a programmed dosage to the user. A rechargeable battery 408 may be provided on the centerline of the barrel inside the flexible circuit. The replaceable insulin cartridge 402 would be located in the lower portion of the pen, and the micro-pump 406 is preferably provided between the insulin cartridge 402 and an infusion needle 410. Micro-pump 406 may be realized by any of the technologies discussed above and provided in the previously incorporated co-pending application titled "Flexible and Conformal Patch Pump" (attorney docket number P-8678 (55581)). In some embodiments, micro-pump 406 may be replaced by a motor provided at the proximal side of the insulin cartridge 402 to drive a movable stopper to directly force fluid into the infusion needle 410. In this embodiment, a linear actuator may be placed inside the flexible circuit in line with an insulin vial. The linear actuator applies a force to drive a plunger or stopper provided in the vial, resulting in a bolus dose equal to the displaced volume of the plunger movement. Very small linear actuators are available and may advantageously be used for this purpose. One example is the Squiggle® linear actuator manufactured by New Scale Technologies. The upper and lower portions of the pen preferably separate in order to replace the insulin cartridge, and when reassembled, provide an electrical connection to the micro-pump 406 or motor. Each time drug delivery device 400 is attached to PDM 500, the rechargeable battery 408 in the delivery device 400 may be charged, and an infusion history or blood glucose history that is stored in the pen may automatically be uploaded to the PDM 500.

An exemplary embodiment of the present invention may provide drug delivery device 400 with the low cost components necessary for communicating via a personal area network as described in previously incorporated, co-pending U.S. patent application Ser. No. 12/458,807. This embodiment enables continued communication between the drug delivery device 400 and PDM 500 or a "smart" wearable medical device as disclosed in the exemplary embodiments above. The "smart" medical device or PDM may automatically program drug delivery device 400 each time a bolus is calculated, as long as both are in physical communication with the user's body. A "smart" wearable medical device containing a biosensor, or otherwise in communication with a biosensor, may also be capable of providing bolus dosage requirements to the drug delivery device 400 to be automatically programmed by the device based on a user's blood glucose level. Additionally, drug delivery device 400 may automatically update via the personal area network, the PDM or "smart" medical device each time a bolus is administered to the user. The above embodiments provide a low-cost, intelligent device capable of further enhancing the functionality of the exemplary wearable medical devices disclosed above, in an embodiment that is easy to use and familiar to many users requiring insulin therapy.

While the present invention has been shown and described with reference to particular illustrative embodiments, it is not to be restricted by the exemplary embodiments but only by the appended claims and their equivalents. It is to be appreciated that those skilled in the art can change or modify the exemplary embodiments without departing from the scope and spirit of the present invention.

What is claimed is:

1. A medical device for administering drug therapy to a user over an extended period of use, said medical device comprising:
   a pump mechanism for administering a drug to the user;
   first and second delivery cannulas for infusing said drug transdermally into the user at first and second infusion sites;
   first and second mechanisms for separately controlling deployment of the first and second cannulas into said user at said first and second infusion sites; and
   a flow sensing unit for detecting whether the first infusion site is no longer viable by sensing whether the first delivery cannula is blocked or otherwise incapable of delivering a desired flow of drug to the user;
   wherein the first delivery cannula is retracted from the user when the flow sensing unit detects that the infusion site is no longer viable.

2. The medical device of claim 1, wherein the first delivery cannula is retracted from the user after a predetermined period of use.

3. The medical device of claim 1, wherein the second delivery cannula is deployed into the user when the first delivery cannula is retracted.

4. The medical device of claim 1, wherein the first and second mechanisms for controlling deployment of the first and second delivery cannulas are manually actuated.

5. The medical device of claim 1, wherein the first and second mechanisms for controlling the deployment of the first and second delivery cannulas are automatically actuated.

6. The medical device of claim 1, further comprising a reservoir supplying a volume of drug necessary for the extended duration of use of the medical device.

7. The medical device of claim 1, further comprising first and second reservoirs for supplying the drug to the respective first and second delivery cannulas.

8. The medical device of claim 1, further comprising a refillable reservoir supplying the drug infused into the user, said reservoir including a port or septum for receiving a supply of the drug.

9. The medical device of claim 1, further comprising a receptacle for receiving a pre-filled reservoir assembly.

10. The medical device of claim 1, wherein the pump mechanism and the first and second mechanisms for controlling deployment of the first and second cannulas are housed in a reusable portion of the medical device.

11. The medical device of claim 1, wherein the medical device is affixed to a user's skin with a flexible, zigzag shaped adhesive strip provided along the perimeter of said medical device.

12. The medical device of claim 11, wherein the adhesive strip comprises an elastomer or foam layer.

13. The medical device of claim 1, wherein the pump mechanism is controlled to administer a preprogrammed drug delivery profile to the user.

14. A medical device for administering drug therapy to a user over an extended period of use, said medical device comprising:
   a pump mechanism for administering a drug to the user;

a delivery cannula for infusing said drug transdermally into the user at an infusion site; and a mechanism for controlling deployment of the cannula into said user, wherein said mechanism is configured to variably move said cannula to a first depth in the user and a second depth in the user; wherein the mechanism is adapted to move the cannula from said first depth to said second depth after said cannula has been at said first depth for at least one day.

15. The medical device of claim 14, wherein the mechanism for controlling deployment of said cannula is configured to retract said cannula after a predetermined period of use and further re-deploy said cannula into said user after a predetermined period of non-use.

16. The medical device of claim 14, wherein the pump mechanism and mechanism for controlling deployment of the cannula are contained in a reusable portion of the medical device.

17. A medical device for administering drug therapy to a user over an extended period of use, said medical device comprising:

a pump mechanism for administering a drug to the user;

a delivery cannula for infusing said drug transdermally into the user at an infusion site; and a mechanism for controlling deployment of the cannula into said user, wherein said mechanism is configured to automatically move said cannula from a first depth in the user to a second depth in the user.

* * * * *